US010907142B2

(12) United States Patent
Zhu et al.

(10) Patent No.: US 10,907,142 B2
(45) Date of Patent: Feb. 2, 2021

(54) OLIGOSACCHARIDES COMPRISING AN AMINOOXY GROUP AND CONJUGATES THEREOF

(71) Applicant: Genzyme Corporation, Cambridge, MA (US)

(72) Inventors: Yunxiang Zhu, Bridgewater, NJ (US); Seng H. Cheng, Natick, MA (US); Canwen Jiang, Southborough, MA (US); Luis Z. Avila, Bridgewater, NJ (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 16/268,989

(22) Filed: Feb. 6, 2019

(65) Prior Publication Data

US 2020/0010825 A1   Jan. 9, 2020

Related U.S. Application Data

(63) Continuation of application No. 15/280,864, filed on Sep. 29, 2016, now abandoned, which is a continuation of application No. 14/272,960, filed on May 8, 2014, now Pat. No. 9,469,850, which is a continuation of application No. 12/523,631, filed as application No. PCT/US2008/051429 on Jan. 18, 2008, now Pat. No. 8,759,501.

(60) Provisional application No. 60/885,471, filed on Jan. 18, 2007.

(51) Int. Cl.
| | |
|---|---|
| *C07H 15/04* | (2006.01) |
| *C12N 9/96* | (2006.01) |
| *C12N 9/16* | (2006.01) |
| *C12N 9/26* | (2006.01) |
| *A61K 47/54* | (2017.01) |
| *A61K 38/47* | (2006.01) |

(52) U.S. Cl.
CPC ............... *C12N 9/96* (2013.01); *A61K 38/47* (2013.01); *A61K 47/549* (2017.08); *C07H 15/04* (2013.01); *C12N 9/16* (2013.01); *C12N 9/2408* (2013.01); *C12Y 301/04012* (2013.01); *C12Y 302/0102* (2013.01); *C12Y 302/01022* (2013.01); *C12Y 302/01076* (2013.01)

(58) Field of Classification Search
None
See application file for complete search history.

(56) References Cited

U.S. PATENT DOCUMENTS

| | | |
|---|---|---|
| 4,671,958 A | 6/1987 | Rodwell et al. |
| 4,701,521 A | 10/1987 | Ryser et al. |
| 5,153,312 A | 10/1992 | Porro |
| 5,206,370 A | 4/1993 | Schwartz et al. |
| 5,212,298 A | 5/1993 | Rademacher et al. |
| 5,280,113 A | 1/1994 | Rademacher et al. |
| 5,306,492 A | 4/1994 | Porro |
| 5,324,663 A | 6/1994 | Lowe |
| 5,420,285 A | 5/1995 | Schwartz et al. |
| 5,521,290 A | 5/1996 | Sivan et al. |
| 5,691,154 A | 11/1997 | Callstrom et al. |
| 5,753,520 A | 5/1998 | Schwartz et al. |
| 6,118,045 A | 9/2000 | Reuser et al. |
| 6,156,547 A | 12/2000 | Roth |
| 6,251,858 B1 | 6/2001 | Monsigny et al. |
| 6,399,575 B1 | 6/2002 | Smith et al. |
| 6,472,506 B1 | 10/2002 | Moreau et al. |
| 6,534,300 B1 | 3/2003 | Canfield |
| 6,537,785 B1 | 3/2003 | Canfield |
| 6,569,451 B1 | 5/2003 | Li et al. |
| 6,573,337 B1 | 6/2003 | Toth et al. |
| 6,642,038 B1 | 11/2003 | Canfield |
| 6,670,165 B2 | 12/2003 | Canfield |
| 6,676,963 B1 | 1/2004 | Lanza et al. |
| 6,723,843 B2 | 4/2004 | Toth et al. |
| 6,749,865 B2 | 6/2004 | Calias et al. |
| 6,770,468 B1 | 8/2004 | Canfield |
| 6,800,472 B2 | 10/2004 | Canfield et al. |
| 6,828,135 B2 | 12/2004 | Canfield |
| 6,861,242 B2 | 3/2005 | Canfield |
| 6,905,856 B2 | 6/2005 | Canfield et al. |
| 7,001,994 B2 | 2/2006 | Zhu |

(Continued)

FOREIGN PATENT DOCUMENTS

| | | |
|---|---|---|
| CA | 1139331 A | 1/1983 |
| EP | 0026823 A1 | 4/1981 |

(Continued)

OTHER PUBLICATIONS

A Guide to IUPAC Nomenclature of Organic Compounds (Recommendations 1993). "Specific Classes of Compounds. R-5.6.6 Nitrogenous derivatives of carbonyl compounds" Blackwell Scientific Publications, [online], [retrieved on Nov. 16, 2009]. Retrieved from the internet <URL http://www.acdlabs.com/iupac/nomenclature/> (6 pages).

(Continued)

Primary Examiner — Layla D Berry

(74) Attorney, Agent, or Firm — Morrison & Foerster LLP

(57) ABSTRACT

The invention provides methods for the synthesis of oligosaccharides comprising an aminooxy group. The invention further provides oligosaccharides comprising an aminooxy group, methods for coupling oligosaccharides comprising an aminooxy group to glycoproteins, and oligosaccharide-protein conjugates. Also provided are methods of treating a lysosomal storage disorder in a mammal by administration of an oligosaccharide-protein conjugate.

1 Claim, 6 Drawing Sheets

(56) References Cited

U.S. PATENT DOCUMENTS

| | | | |
|---|---|---|---|
| 7,019,131 | B2 | 3/2006 | Wong et al. |
| 7,067,127 | B2 | 6/2006 | Canfield |
| 7,160,517 | B2 | 1/2007 | Seeberger et al. |
| 7,176,185 | B2 | 2/2007 | Hilfinger et al. |
| 7,341,720 | B2 | 3/2008 | Stefano |
| 7,723,296 | B2 | 5/2010 | Zhu |
| 8,124,073 | B2 | 2/2012 | Stefano |
| 8,399,657 | B2 | 3/2013 | Zhu |
| 8,759,501 | B2 | 6/2014 | Zhu et al. |
| 8,841,427 | B2 | 9/2014 | Zhu et al. |
| 8,906,379 | B2 | 12/2014 | Stefano |
| 9,469,850 | B2 | 10/2016 | Zhu et al. |
| 9,498,518 | B2 | 11/2016 | Stefano |
| 9,687,531 | B2 | 6/2017 | Zhu |
| 10,363,291 | B2 | 7/2019 | Zhu |
| 2002/0025550 | A1 | 2/2002 | Canfield |
| 2002/0137125 | A1 | 9/2002 | Zhu |
| 2003/0050299 | A1 | 3/2003 | Hirth et al. |
| 2003/0082176 | A1 | 5/2003 | Lebowitz et al. |
| 2003/0087868 | A1 | 5/2003 | Yew et al. |
| 2003/0119088 | A1 | 6/2003 | Canfield et al. |
| 2004/0006008 | A1 | 1/2004 | Lebowitz et al. |
| 2004/0132640 | A1 | 7/2004 | Defrees et al. |
| 2005/0003486 | A1 | 1/2005 | Canfield et al. |
| 2005/0026823 | A1 | 2/2005 | Zankel et al. |
| 2005/0048047 | A1 | 3/2005 | Kakkis |
| 2005/0058634 | A1 | 3/2005 | Zhu |
| 2005/0169941 | A1 | 8/2005 | Lees |
| 2005/0169968 | A1 | 8/2005 | Elmaleh et al. |
| 2005/0222244 | A1 | 10/2005 | Siegel et al. |
| 2005/0267094 | A1 | 12/2005 | Shayman et al. |
| 2005/0281805 | A1 | 12/2005 | Lebowitz et al. |
| 2006/0051317 | A1 | 3/2006 | Batrakova et al. |
| 2006/0281145 | A1 | 12/2006 | Zhu |
| 2007/0191263 | A1 | 8/2007 | Jones et al. |
| 2009/0022702 | A1 | 1/2009 | Zhu |
| 2010/0047225 | A1 | 2/2010 | Zhu et al. |
| 2010/0173385 | A1 | 7/2010 | Zhu |
| 2010/0317609 | A1 | 12/2010 | Norbert et al. |
| 2011/0300120 | A1 | 12/2011 | Avila et al. |
| 2017/0042979 | A1 | 2/2017 | Stefano |
| 2018/0085436 | A1 | 3/2018 | Zhu |
| 2019/0054154 | A1 | 2/2019 | Stefano |

FOREIGN PATENT DOCUMENTS

| | | |
|---|---|---|
| EP | 0384769 A2 | 8/1990 |
| EP | 2457920 A1 | 5/2012 |
| JP | 2002-539294 A | 11/2002 |
| JP | 2003-501412 A | 1/2003 |
| JP | 2006-511635 A | 4/2011 |
| JP | 2015-78360 A | 4/2015 |
| WO | WO-92/16555 A1 | 10/1992 |
| WO | WO-00/055210 A1 | 9/2000 |
| WO | WO-01/60412 A2 | 8/2001 |
| WO | WO-01/90139 A2 | 11/2001 |
| WO | WO-02/07671 A2 | 1/2002 |
| WO | WO-03/031464 A2 | 4/2003 |
| WO | WO-03/057179 A2 | 4/2003 |
| WO | WO-2005/002515 A2 | 1/2005 |
| WO | WO-2005/014035 A2 | 2/2005 |
| WO | WO-2005/016973 A1 | 2/2005 |
| WO | WO-2005/034909 A2 | 4/2005 |
| WO | WO-2005/072778 A2 | 8/2005 |
| WO | WO-2005/077093 A2 | 8/2005 |
| WO | WO-2005/094874 A1 | 10/2005 |
| WO | WO-2008/089339 A2 | 7/2008 |
| WO | WO-2008/089339 A3 | 7/2008 |
| WO | WO-2008/089403 A2 | 7/2008 |

OTHER PUBLICATIONS

Abraham et al., "Heparin-Binding EGF-Like Growth Factor: Characterization of Rat and Mouse cDNA Clones, Protein Domain Conservation Across Species, and Transcript Expression in Tissues" Biophys. Res. Commun. 190(1):125-133 (1993).

Amalfitano et al., "Systemic Correction of the Muscle Disorder Glycogen Storage Disease Type II After Hepatic Targeting of a Modified Adenovirus Vector Encoding Human Acid-a-Glucosidase" Proc. Nati. Acad. Sci. USA 96 8861-8866 (Aug. 1999).

Arakatsu et al., "Immunochemical Studies on Dextrans. V. Specificity and Cross-Reactivity with Dextrans of the Antibodies Formed in Rabbits to Isomaltonic and Isomaltotrionic Acids Coupled to Bovine Serum Albumin" J. Immunol. 97(6):858-866 (1966).

Ashwell et al. "Carbohydrate-specific Receptors of the Liver" Ann. Rev. Biochem. 51:531-534 (1982).

Avigad et al., "The D-Glactose Oxidase of Polyporus circinatus" J. Biol. Chem. 237(9):2736-2743 (1962).

Baba et al. "Preparation and Application of a Pentamannosyl Monophosphate-Bovine Serum Albumin Conjugate" Carbohydrate Research 177:163-172 (1988).

Bala.Ji et al , "Molecular dynamics simlulations of high-mannose oligosaccharides" Glycobiology 4(4):497-515 (Aug. 1994).

Bandyopadhyay et al. Nucleotide Exhange in Genomic DNA of Rat Hepatocytes Using RNA/DNA I Oligonucleotides, J. Biol. Chem. 274(15):10163-10172 (1999).

Bayer et al., "Biocytin Hydrazide—A Selective Label for Sialic Acids, Galactose, and Other Sugars in Glycoconjugates Using Avidin-Biotin Technology" Analyt. Biochem. 170:271-281 (1988).

Beesley et al., "Mutational analysis of 85 mucopclysaccharidosis type I families: frequency of known mutations, identification of 17 novel mutations and in vitro expression of missense mutations" Hum. Genet. 109(5):503-511 (Nov. 2011; epub Oct. 19, 2001).

Berge et al,, "Pharmaceutical Salts" J. Pharm. Sci. 66:1-19 (19T7).

Bernstein et al., "A general synthesis of model glycoproteins: coupling of alkenyl glycosides to proteins, using reductive ozonolysis followed by reductive amination with sodium cyanoborohydride" Carbohydrate Research 78:C1-C3 (1980).

Bijvoet et al., "Human acid α-glucosidase from rabbit milk has therapeutic effect in mice with glycogen storage disease type II" Hum. Mol. Genet. 8(12):53-62 (1998).

Bijvoet et al.; "Generalized Glycogen Storage and Cardiomegaly in a Knockout Mouse Model of Pompe Disease" Hum. Mol. Genet. 7(1):53-62 (1998).

Bond et al., "Structure of a human lysosomal sulfatase" Structure 5:277-289 (Feb. 1997).

Branden et al., Introduction to Protein Structure. 2ed. Garland Publishing, Inc., New York: 1999; pp. 358-366.

Braslawsky et al., "Adriamycin(hydrazine)-antibody conjugates require internalization and intracellular acid hydrolysis for antitumor activity" Cancer Immunol. Immunother. 33:367-374 (1991).

Bretthauer et al., "Characterization of a Phosphorylated Pentasaccharide Isolated from Hansenula holstii NRRL Y-2448 Phosphomannan" Biochemistry 12(7): 1251-1256 (1973).

Brooks et al., "A specific fluorogenic assay for N-acetylgaiactosamine-4-sulphatase activity using immunoadsorption" J. Inher. Metab. Dis. 14:5-12 (1991).

Brooks et al., "Glycosidase active site mutations in human α-L-iduronidase" Glycobiology 11(9):741-750 (2001).

Caliceti et al., "Pharmacokinllic and Biodistribution Properties of Poly( ethylene glycol)-Protein Conjugates" Advanced Drug Delivery Reviews 55:1261-1277 (2003).

Casares et al., Antigen-specific dowmegulation of T cells by doxorubicin delivered through a recombinant MHC II-peptide chimera; Nat. Biotechnol. 19:142-14'7 (2001).

Cavallaro et al. "Glycosilated Macromolecular Conjugates of Antiviral Drugs with a Polyaspartamide" J. Drug Targeting 12(9-10):593-605 (2004).

Chaudhari et al., "Coupling of Amino Acids and Amino Sugars with Cyanuric Chloride (2,4,6-Trichloro-s-triazine)" Can. J. Chem. 50(13):1987-1991 (1972).

Chen, et al., "Purification and Characterization of Human a-Galactosidase A Expressed in Insect Cells Using a Baculovirus Vector", Protein Expr. Purif. 20:228-2236 (2000).

(56) References Cited

OTHER PUBLICATIONS

Chen et al., "Towards a Molecular Therapy for Glycogen Storage Disease Type II (Pompe Disease)" Molecular Medicine Today 6(6):245-251 (Jun. 2000).
Civallero et al., "Twelve different enzyme assays on dried blood filter paper samples for detection of patients with selected inherited lysosomal storage diseases" Clin. Chim. Acta 372:98-102 (2006).
Cole-Strauss et al., "Correction of the Mutation Responsible for Sickle Cell Anemia by an RNA/DNA Oligonucleotide," Science 273(5280):1386-1389, (Sep. 6, 1996).
Crich et al., "Direct Chemical Synthesis of β-Mannopyranosides and Other Glycosides via Glycosyl Triflates" Tetrahedron 54:8321-8348 (1998).
Davis et al, "Glycoprotein Synihesis: From Glycobiological Tools to Tailor-made Catalysis" Syniett 9:1495-1507 (1999).
Davis, "Recent Developments in Glycoconjugates" J. Cfiem. Soc., Perkin Trans. 1. 1:3215-3237 (1999).
Davis, "Synthesis of Glycoproteins" Chem. Rev. 102:579-601 (2002).
Day et al., "Induction of Antigen-Specific CTL Responses Using Antigens Conjugated to Short Peptide Vectors" J. Immunol. 170:1498-1503 (2003).
Demeule et al., "High transcytosis of melanotransferrin (P97) across the blood-brain barrier" J. Neurochem. 83:924-933 (2002).
Derossi et al., "Trojan peptides: the penetratin system for intracellular delivery" Trends Cell Biol. 8:84-87 (1998).
Di Francesco et al., "In vitro correction of iduronate-2-sulfatase deficiency by adenovirus-mediated gene transfer" Gene Ther. 4(5):442-448 (1997).
Distler et al. "The Binding Specificity of High and Low Molecular Weight Phosphomannosyl Receptors from Bovine Testes: inhibition Studies with Chemically Synthesized 6-0-phosphorylated Oligomannosides" J. Biol. Chem. 266(22):21687-21692 (1991).
Downing et al., "Synthesis of enzymaticaliy active human a-L-iduronidase in Arabidopsis cgl (Complex glycandeficient) seeds" Plant Biotechnol. 4(2): 169-181 (2006).
Duffels et al., "Synthesis of high mannose type neoglycolipids: active targeting of liposomes to macrophages in gene therapy" Chem. Eur. J. 6(8): 1416-1430 (2000).
Duncan et al, "A New Reagent Which May Be Used to Introduce Sulfhydryl Groups Into Proteins, and Its Use in the Preparation of Conjugates for Immunoassay" Anal. Biochem. 132:68-73 (1983).
Durand et al., "Active-site motifs of lysosomal acid hydrolases: invariant features of clan GH-A glycosyl hydrolases deduced from hydrophobic cluster analysis" Glycobiology 7(2): 277-284 (1997).
Dvir et al., "X-ray structure of human acid-β-glucosidase, the defective enzyme in Gaucher disease" EMBO Reports 4(7): 1-6 (2003).
Elliott et al., "Intercellular Trafficking and Protein Delivery by a Herpesvirus Structural Protein" Cell 88:223-233(1997).
Etrych et al., "New HPMA copolymers containing doxorubicin bound via pH-sensitive linkage: synthesis and preliminary in vitro and in vivo biological properties" J. Controlled Release 73: 89-102 (2001).
European Patent Application No. 06740572.0: Summons to Attend Oral Proceedings at the European Patent Office, dated Mar. 30, 2011.
Fawell et al., "Tat mediated delivery of heterologous proteins into cells" Proc. Natl. Acad. Sci. U.S.A. 91:664-668 (Jan. 1994).
Fielder et al., "An Immunogenic Polysaccharide-Protein Conjugate" J. Immunol. 105(1):265-267 (1970).
Final Office Action dated Jul. 19, 2016, for U.S. Appl. No. 14/463,955, filed Aug. 20, 2014, 5 pages.
Flomen et al, "Determination of the organization of coding sequences within the iduronate sulphate sulphatase (IDS) gene" Hum. Mol. Genet. 2:5-10 (1993).
Fujita et al., "Targeted Delivery of Human Recombinant Superoxide Dimutase by Chemical Modification with Mono- and Polysaccharide Derivatives" J. Pharmacol. Exp. Ther. 263(3):971-978 (1992).
Furbish et al., "Uptake and Distribution of Placental Glucocerebrosidase in Rat Hepatic Cells and Effects of Sequential Deglycosylation" Biochim, Biophys. Acta 673:425-434 (1981).
Gahmberg et al. "Nonmetabolic Radiolabelling and Tagging of Glycoconjugates" Meth. Enzymol. 230:32-45 (1994).
Gahmberg et al, "Cell surface carbohydrate in cell adhesion. Sperm cells and leukocytes bind to their target cells through specific oligosaccharide ligands" APMIS Suppl. 27(100):39-52 (1992).
Garman et al., "Structural Basis of Fabry Disease" Mol. Genet. Metabol. 77(1-2):3-11 (2002).
Garman et al., "The Molecular Defect Leading to Fabry Disease: Structure of Human α-Galactosidase" J. Mol. Biol. 337:319-335 (2004).
GenBank Accession No. A1587087, "tr53a08.x1 NC_CGAP_Pan1 *Homo sapiens* cDNA clone IMAGE: 2222006 3—similar to gb:X59960 Sphingomyelin Phosphodiesterase Precursor (Human): mRNA sequence" (1997).
GenBank Accession No. NM_000152, "*Homo sapiens* glucosidase, alpha; acid (GAA), transcript variant 1, mRNA" (2006).
Gen Bank Accession No. X05790, "Human mRNA for alpha-galactosidase A (EC 3.2. 1-22)" (1987).
Geoghegan et al., "Site-Directed Conjugation of Nonpeptide Groups to Peptides and Proteins via Periodate Oxidation of a 2-Amino Alcohol. Application to Modification at N-Terminal Serine" Bioconjugate Chem. 3:138-146 (1992).
Ghose et al., "Preparation of Antibody-Linked Cytotoxic Agents" Meth. Enzymol. 93:280-333 (1983).
Gottschalk et al, "Folate receptor mediated DNA delivery into tumor cells: potosomal disruption results in enhanced gene expression" Gene Ther. 1:185-191 (1994).
Gray, "The Direct Coupling of Oligosaccharides to Proteins and Derivatized Gels" Arch. Biochem. Biophys. 163:426-428 (1974).
Gregoriadis et al., "Polysialic acids: potential in drug delivery" FEBS 315(3):2'11-276 (Jan. 1993).
Gregoriadis et al, "Poiysialylated proteins. An approach to improving enzyme stability and half-life in the blood circulation" S.T.P. Pharma Sci. 9(1):61-66 (1999).
Hagihara et al., "Exploration of oligosaccharide-protein interaction in glycoprotein quality control by synthetic approaches" Chem. Rec. 6(6):290-302 (2006).
Helenius et al., "Intracellular Functions of N-Linked Glycans" Science 291(5512):2364-2369 (Mar. 2001).
Heng et al., "Synthesis of a mannotetraoise—the repeating unit of the cell-wall mannans of Microsporum gypseum and related species of Trychophyton" J. Carb. Chem. 20(3-4):285-296 (2001).
Himmelspach et al., "Use of 1-(m arninophenyl) flavazoles for preparation of immunogens with oligosaccharide determinant groups" Eur. J. Immunol. 1(2)106-112 (1971).
Hinman et al., "Preparation and Characterization of Monoclonal Antibody Conjugates of the Calichearnicins: A Novel and Potent Family of Antitumor Antibiotics" Cancer Res. 53:3336-3342 (1993).
Hodosi et al., "A Fundamentally New, Simple, Sterospecific Synthesis of Oligosaccharides Containing the β-Mannopyranosyl and β-Rhamnopyranosyl Linkage" J. Am. Chem. Soc. 119:2335-2336 (1997).
Hoefsloot et al., "Characterization of the human lysosomal α-glucosidase gene" Biochem. J. 272:493-497 (1990).
Hoefsloot et al., "Primary structure and processing of lysosomal α-glucosidase; homology with the intestinal sycrase-isomaltase complex" EMBO J. 7(6):1697-1704 (1986).
Hojo et al., "Recent Progress in the Solid-phase Synthesis of Glycopeptide" Current Prot. Peptide Sci. 1:23-48 (2000).
Horinouchi et al., "Acid sphingomyelinase deficient mice: a model of types A and B Niemann-Pick disease" Nat. Genet. 10:288-293 (1995).
International Search Report and Written Opinion issued in International Patent Application No. PCT/US2006/012698; dated Nov. 10, 2006.
International Search Report and Written Opinion issued in Application No. PCT/US2008/051429; dated Oct. 7, 2008.
Ioannou et al. "Overexpression of Human a-Galactosidase α-Galactosidase-Galactosidase A Results in Its Intracellular Aggre-

(56) References Cited

OTHER PUBLICATIONS gation, Crystallization Lysosomes, and Selective Secretion" J. Cell Biol. 119(5):1137-1150 (Dec. 1992).

Ioannou et al., "Fabry Disease: Preclinical Studies Demonstrate the Effectiveness of a α-Galactosidase A Replacement in Enzyme-Deficient Mice" Am. J. Hum. Genet. 68:14-25 (2001).

Japanese Notification of Reasons for Refusal dated Nov. 6, 2015, for JP Application No. 2014-204593 filed Jan. 18, 2008; 9 pages.

Japanese Notification of Reasons for Refusal dated Feb. 9, 2016, for JP Application No. 2009-546533 filed Jan. 18, 2008; 3 pages.

Jeyakumar et al., "Enhanced Survival in Sandhoff Disease Mice Receiving a Combination of Substrate Deprivation Therapy and Bone Marrow Transplantation" Blood 97(1):327-329 (Jan. 2001).

Jeyakumar et al. "Glycosphingolipid lysosomal storage diseases: therapy and pathogenesis" Neuropath. Appl. Neurobiol. 28:343-357 (2002).

Kakkis et al., "Overexpression of the Human Lysosomal Enzyme α-L-iduronidase in Chinese Hamster Ovary Cells" Prot. Express. Purif. 5:225-232 (1994).

Kakkis et al, "Successful Induction of Immune Tolerance to Enzyme Replacement Therapy in Canine Mucopolysaccharidosis I" PNAS 101 (3):829-834 (2004).

Kamada et al., "Synthesis of poly(vinylpyrrolidone-co-dimethyl maleic anhydride) co-polymer and its application for renal drug targeting" Nat. Biotechnol. 21:399-404 (Apr. 2003).

Kaneko et al., "New Hydrazone Derivatives of Adriamycin and Their lmmunoconjugates-a Correlation between Acid Stability and Cytotoxicity" Bioconjugate Chem. 2(3):133-141 (1991).

Kikuchi et al., "Clinical and Metabolic Correction of Pompe Disease by Enzyme Therapy in Acid Maltase-deficient Quail" J. Clin. Invest. 101(4):827-833 (1998).

Kim et al., "Mutational spectrum of the iduronate 2 sulfatase gene in 25 unrelated Korean Hunter syndrome patients: identification of 13 novel mutations" Hum. Mutat. 21:449-450 (2003).

Kim et al., "Stereoselective direct glycosylation with anomeric hydroxy sugars by activation with phthalic anhydride and trifluoromethanesulfonic anhydride involving glycosyl phthalate intermediates" J. Am. Chem. Soc. 130:8537-8547 (2008).

King et al., "Monoclonal Antibody Conjugates of Doxorubicin Prepared with Branched Linkers: A Novel Method for Increasing the Potency of Doxorubicin Immunoconjugates" Bioconjugate Chem. 10:279-288 (1999).

King et al., "Preparation of Protein Conjugates via Intermolecular Hydrazone Linkage" Biochemistry 25:5774-5779 (1986).

Kleinhammer et al., "Synthesis and immunological properties of an artificial antigen with the repeating oligosaccharide unit of *Salmonella* Illinois as haptenic group" Eur. J. Immunol. 3:834-843 (1973).

Kmiec. "Genetic Manipulation in Mammalian Cells Using an RNA/DNA Chimeric Oligonucleotide" Adv. Drug Deliv. Rev. 17:333-340 (1995).

Kornfeld et al., "The Biogenesis of Lysosomes" Annu. Rev. Cell Biol. 5:483-525 (1989).

Kralovec et al. "Synthesis of site-specific methotrexate-IgG conjugates. Comparison of stability and antitumor activity with active-ester based conjugates" Cancer Immunol. Immunother. 29:293-302 (1989).

Kren et al.,. "In Vivo Site-Directed Mutagenesis of the Factor *IX* Gene by Chimeric RNA/DNA Oligonucleotides," Nature Med. 4(3):285-290 (Mar. 1998).

Kren et al., "Correction of the UDP-Glucuronosyltransferase Gene Defect in the Gunn Rat Model of Crigler-Naiiar Syndrome Type I with a Chimeric Oligonucleotide," Proc. Natl. Acad. Sci. USA 96:10349-10354 (Aug. 1999).

Lansmann et al., "Human acid sphingomyelinase. Assignment of the disulfide bond pattern" Eur. J. Biochem. 270:1076-1088 (2003).

Lebowitz et al., "Glycosylation-independent targeting enhances enzyme delivery to lysosomes and decreases storage in mucopolysaccharidosis type VII mice" PNAS 101(9):3083-3088 (Mar. 2004).

Lecolley et al., "A new approach to bioconjugates for proteins and peptides ("pegylation") utilizing living radical polymerisation" Chem. Commun. 18:2026-2027 (2004).

Lee et al., "2-Imino-2-Methoxyethyl 1-Thioglycosides: New Reagents for Attaching Sugars to Proteins" Biochemistry 15(18):3956-3963 (1976).

Lee et al., "A Biochemical and Pharmacological Comparison of Enzyme Replacement Therapies for the Glycolipid Storage Disorder Fabry Disease" Glycobiology 13(4):305-313 (2003).

Lee et al., "N-Terminal Site-Specific Mono-PEGylation of Epidermal Growth Factor" Pharm. Res. 20(5):818-825 (May 2003).

Lee et al., "Receptor mediated uptake of peptides that bind the human transferrin receptor" Eur. J. Biochem. 268:2004-2012 (2001).

Lees et al., "Versatile and efficient synthesis of protein-polysaccharide conjugate vaccines using aminooxy reagents and oxime chemistry," Vaccine 24:716-729. (2006).

Lemieux et al., "The Properties of a 'Synthetic' Antigen Related to the Human Blood-Group Lewis a" J. Am. Chem. Soc. 97(14):4076-4083 (1975).

Li et al., "Direct Multiplex Assay of Lysosomal Enzymes in Dried Blood Spots for Newborn Screening" Clin. Chem. 50(10):'1785-1796 (2004).

Li et al., "Isolation and Characterization of Mannose 6-Phosphate/Insulin-Like Growth Factor II Receptor from Bovine Serum" Glycobiol. 1(5):511-517 (1991).

Liou et al., "Analyses of Variant Acid β-Glucosidases. Effects of Gaucher Disease Mutations" J. Biol. Chem. 281(7):4242-4253 (Feb. 2006).

Lisi et al., "Enzyme Therapy. I. Polyethylene Glycol:,β-Glucumnidase Conjugates as Potential Therapeutic Agents in Acid Mucopolysaccharidosis" J. Appl. Biochem. 4:19-33 (1982).

Litjens et al., "An N-acetylgalactosarnine-4-sulfatase mutation (Δ Gna) results in a severe Maroteaux-Lamy phenotype" Hum. Mut. 1(5):397-402 (1992).

Lovering et al., "Mechanistic and Analysis of a Family 31 α-Glycosidase and its glycosyl-enzyme Intermediate" J. Biol. Chem. 280(3):2105-2115 (2005).

MacDermott et al., "Anderson-Fabry disease: clinical manifestations and impact of disease in a cohort of 98 hemizygous males" J. Med. Genet. 38:750-760 (2001).

Mann et al., "Endocytosis and targeting of exogenous HIV-1 Tat protein" EMBO J. 10(7):1733-1739 (1991).

Marshall et al., "Demonstration of Feasibility of In Vivo Gene Therapy for Gaucher Disease Using a Chemically Induced Mouse Model" Mol. Ther. 6(2):179-189 (Aug. 2002).

Martiniuk et al., "Isolation of a cDNA for human acid α-glucosidase and detection of genetic heterogeneity for mRNA in three α-glucosidase-deficient patients" Proc. Natl. Acad. Sci. USA 83:9641-9644 (1986).

Matsuura et al., "Human α-Galactosidase A: Characterization of the N-Linked Oligosaccharides on the Intracellular and Secreted Glycoforms Overexpressed by Chinese Hamster Ovary Cells" Glycobioiogy 8(4):329-339 (1998).

Matsuzawa et al., "Fabry disease: correlation between structural changes in α-glucosidase, and clinical and biochemical phenotypes" Hum. Genet. 117:317-328 (2005).

Mayer et al., "Synthesis of Labeled Glycosyl Phosphatidyl Inositol (GPI) Anchors" Eur. J. Org. Chem. 1999(10):2563-2571 (1999).

Mayes et al., "Differential assay for lysosomal α-galactosidases in human tissues and its application to Fabry's disease" Clin. Chim. Acta 112:247-251 (1981).

McBroom et al., "Carbohydrate Antigens: Coupling of Carbohydrates to Proteins by Diazonium and Phenylisothiocyanate Reactions" Methods in Enzymology. vol. XXVIII, Complete Carbohydrates, Part B pp. 212-219 (1972).

McVie-Wylie et al., "Biochemical and pharmacological characterization of different recombinant acid α-glucosidase preparations evaluated for the treatment of Pompe disease" Mol. Genet. Metab. 94:448-455 (2008).

Medin et al., "Correction in trans for Fabry disease: Expression, secretion and uptake of α-glucosidase A in patient-derived cells driven by a high-titer recombinant retroviral vector," Proc. Natl. Acad. Sci. USA 93:7917-7922 (1996).

(56) References Cited

OTHER PUBLICATIONS

Menander-Huber et al., "Orgotein, the Drug Version of Bovine Cu—Zn Superoxide Dismutase II A Summary Account of Clinical Trials in Man and Animals" in Superoxide and Superoxide in Dismutases. A.M. Michelson et al. (eds.), Academic Press, 1977: pp. 537-549.

Minko et al., "Molecular Targeting of Drug Delivery Systems to Cancer" Current Drug Targets 5:389-406 (2004).

Mitchell et al., "Polyarginine enters cells more efficiently than other polycationic homopolymers" J. Peptide Res. 56:318-325 (2000).

Mizukami et al., "Systemic inflammation in glucocerebrosidase-deficient mice with minimal glucosylceramide storage" J. Clin. Invest. 109:1215-1221 (2002).

Michelson, ed. et al. "Production of Superoxide by Metal Ions," *Superoxide and Superoxide Dismutases*, United States Edition, Academic Press Inc., New York, New York, 77-86, 12 pages, (1977).

Moczar et al., "Preparation of N-Acetylglucosamine Derivatives of Proteins" FEBS Letters 50(3):300-302 (1975).

Molema et al. "Neoglycoproteins as Carriers for Antiviral Drugs: Synthesis of Analysis of Protein-Drug Conjugates" J. Med. Chem. 34:1137-1141 (1991).

Montalvo et al., "Glycogenosis type II: identification and expression of three novel mutations in the acid a-glucosidase gene causing the infantile form of the disease" Mol. Genet. Metab. 81:203-208 (2004).

Moreland et al., "Lysosomal Acid α-Glucosidase Consists of Four Different Peptides Processed from a Single Chain Precursor" J. Biol. Chem. 280(8):6780-6791 (2005).

Munier-Lehmann et al., "Re-expression of the Mannose 6-Phosphate Receptors in Receptor-deficient Fibroblasts" J. Biol. Chem. 271(25):15166-15174 (1996).

Murray et al., "Cellular and Tissue Distribution of Intravenously Administered Agalsidase Alfa" Author manuscript [online].

Murunganandam et al., "Selection of phage-displayed llama single-domain antibodies that transmigrate across human blood-brain barrier endothelium" FASEB J. 16:240-242(2002).

Mutsaers et al., "Determination of the structure of the carbohydrate chains of acid α-glucosidase from human placenta" Biochim. Biophys. Acta 911:244-251 (1987).

Nicolaou et al. "New Synthetic Technology for the Stereocontrolled Construction of 1,1-Disaccharides and 1,1':1,2-Trisaccharides. Synthesis of the FG Ring System of Everninomicin 13,384-1" J. Am. Chem. Soc. 119:9507-9508 (1997).

Nieman et al., "Family 39 α-L-iduronidases and β-D-xylosidases react through similar glycosyl-enzyme intermediates: identification of the human iduronidase nucleophile" Biochemistry 42(26):8054-8065 (Jul. 2003).

Notice of Allowance dated Jun. 3, 2014, for U.S. Appl. No. 13/768,266, filed Feb. 15, 2013, 8 pages.

Notice of Allowance dated Aug. 8, 2014, for U.S. Appl. No. 13/354,855, filed Jan. 20, 2012, 8 pages.

Notice of Allowance dated Jul. 14, 2016, for U.S. Appl. No. 14/534,328, filed Nov. 6, 2014, 7 pages.

Notice of Allowance dated Feb. 22, 2017, for U.S. Appl. No. 14/463,955, filed Aug. 20, 2014, 8 pages.

Office Action dated Oct. 22, 2013, for U.S. Appl. No. 13/768,266, filed Feb. 15, 2013, 6 pages.

Office Action dated Apr. 9, 2014, for U.S. Appl. No. 13/354,855, filed Jan. 20, 2012, 11 pages.

Office Action dated Feb. 19, 2016, for U.S. Appl. No. 14/534,328, filed Nov. 6, 2014, 5 pages.

Office Action dated Mar. 23, 2016, for U.S. Appl. No. 14/463,955, filed Aug. 20, 2014, 7 pages.

Office Action dated Dec. 13, 2017, for U.S. Appl. No. 15/280,864, filed Sep. 29, 2016, 6 pages.

Office Action dated Jan. 29, 2018, for U.S. Appl. No. 15/297,083, filed Oct. 18, 2016, 11 pages.

Ohkuma et al., "Fluorescence probe measurement of the intralysosomal pH in living cells and the perturbation of pH by various agents" Proc. Natl. Acad. Sci. USA 75(7):3327-3331 (1978).

Ohshima et al., "α-Galactosidase A deficient mice: A model of Fabry disease" Proc. Natl. Acad. Sci. USA 94:2540-2544 (Mar. 1997).

Olson et al. (Oct. 1999). "Structural Basis for Recognition of Phosphorylated High Mannose Oligosaccharides by the Cation-dependent Mannose 6-Phosphate Receptor" J. Biol. Chem. 274(42) 29886-29889.

Olson et al., "Structure of uPAR, plasminogen, and sugar-brinding sites of the 300 kDa mannose 6-phosphate receptor" EMBO J. 23:2019-2028 (2004).

Olson et al., "The N-terminal Carbohydrate Recognition Site of the Cation-independent Mannose 6-Phosphate Receptor" J. Biol. Chem. 279(32):34000-34009 (Aug. 2004).

Olson et al., "Twists and Turns of the Cation-dependent Mannose 6-Phosphate Receptor" J. Biol. Chem. 277(12):10156-10161 (Mar. 22, 2002).

Orr et al., "Synthetic Concanavalin A Receptors and Erythrocyte Agglutination" Nature 272:722-725 (1978).

O'Shannessy et al., "A Novel Procedure for Labeling Immuno-globulins by Conjugation to Oligosaccharide Moieties" Immunol. Lett. 8:273-277 (1984).

O'Shannessy et al., "Specific Conjugation Reactions of the Oligosaccharide Moieties of Immunoglobulins" J. Applied Biochem. 7:347-355 (1985).

Papisov et al., "Hydrophilic Polyals: Biomimetic Biodegradable Stealth Materials for Pharmacology and Bioengineering" Abstract, 226th American Chemical Society National Meeting. New York, NY, Sep. 7-11, 2003.

Papisov et al., "Semisynthetic Hydrophilic Polyals" Biomacromolecules 6:2659-2670 (2005).

Papisov, "Acyclic polyacetals from polysaccharides" ACS Symposium Series 786:301-314 (2001).

Parolis et al., "The Extracellular Polysaccharide of Pichia (Hansenula) holstii NRRL Y-2448: The Phosphorylated Side Chains" Carbohydr. Res. 309: 77-87 ( 1998).

Pekari et al, "Synthesis of the fully phosphoryiated GPI anchor pseudohexasaccharide of Toxoplasma gondii" J. Org. Chem. 66:7432-7442 (2001).

Peters et al., "Phylogenetic Conservation of Aryisulfatases. cDNA Cloning and Expression of Human Arylsulfatase B" J. Biol. Chem. 265(6):3374-3381 (Feb. 1990).

Poznansky et al., "Insulin Carrier Potential for Enzyme and Drug Therapy" Science 223:1304-1306 (1984).

Poznansky et al., "α-1,4-Glucosidase-albumin polymers: in vitro properties and advantages for enzyme replacement therapy" Can. J. Physiol. Pharmacol. 58:322-325 (1980).

Prince et al., "Lipoprotein Receptor Binding, Cellular Uptake, and Lysosomal Delivery of Fusions between the Receptor-associated Protein (RAP) and α-L-Iduronidase or Acid α-Glucosidase" J. Biol. Chem. 279(33):35037-35046 (Aug. 2004).

Qiu et al., "Activation of Human Acid Sphingomyelinase through Modification or Deletion of C-terminal Cysteine" J. Biol. Chem. 278(35):32744-32752 (Aug. 2003).

Raben et al., "Targeted Disruption of the Acid a-Glucosidase Gene in Mice Causes an Illness with Critical Features of Both Infantile and Adult Human Glycogen Storage Disease Type II", J. Biol. Chem. 273(30):19086-19092, (Jul. 24, 1998).

Raben et al., "Enzyme Replacement Therapy in the Mouse Model of Pompe Disease" Mol. Genet. Metab.80:159-169 (2003).

Raben et al., "Glycogen Stored in Skeletal but Not in Cardiac Muscle in Acid a-Glucosidase Mutant (Pompe) Mice is Highly Resistant to Transgene-Encoded Human Enzyme" Mol. Ther. 6(5):601-608 (Nov. 2002).

Raben et al., "Replacing Acid a-Glucosidase in Pompe Disease: Recombinant and Transgenic Enzymes Are Equipotent, but Neither Completely Clears Glycogen from Type II Muscie Fibers" Mol. Ther. 11:48-56 (2005).

Rando et al., "Rescue of Dystrophin Expression in *mdx* Mouse Muscle by RNA/DNA Oligonucleotides", Proc. Natl. Acad. Sci. USA 97:5363-5368, (2000).

(56) References Cited

OTHER PUBLICATIONS

Rempel et al, "A homology model for human a-L-iduronidase: insights into human disease" Mol. Genet. Metab. 85:28-37 (2005).
Restriction Requirement dated Aug. 8, 2006, for U.S. Appl. No. 11/398,949, filed Apr. 5, 2006, 14 pages.
Restriction Requirement dated Sep. 1, 2009, for U.S. Appl. No. 11/970,907, filed Jan. 8, 2008, 11 pages.
Restriction Requirement dated Dec. 20, 2013, for U.S. Appl. No. 13/354,855, filed Jan. 20, 2012, 9 pages.
Restriction Requirement dated Nov. 27, 2015, for U.S. Appl. No. 14/534,328, filed Nov. 6, 2014, 8 pages.
Restriction Requirement dated Oct. 13, 2017, for U.S. Appl. No. 15/297,083, filed Oct. 18, 2016, 8 pages.
Reuser et al., "Uptake and Stability of Human and Bovine Acid a-Glucosidase in Cultured Fibroblasts and Skeletal Muscle Cells from Glycogenosis Type II Patients" Exp. Cell Res. 155(1):178-189 (1984).
Rodriguez et al., "A Strategy for the Chernoselective Synthesis of 0-Linked Glycopeptides with Native Sugar-Peptide Linkages" J. Am. Chem. 119(4):9905-9906 (1997).
Rodriguez, E.C. et al. (Oct. 1, 1998). "Aminooxy-, Hydrazide-, and Thiosemicarbazide-Functionalized Saccharides: Versatile Reagents for Glycoconjugate Synthesis," J. Org. Chem. 63:7134-7135.
Rodwell et al., "Site-specific covalent modification of monoclonal antibodies: In vitro and in vivo evaluations" Proc. Natl. Acad. Sci USA 83:2632-2636 (1986).
Roussele et al, "New Advances in the Transport of Doxorubicin through the Blood-Brain Barrier by a Peptide Vector-Mediated Strategy" Mol. Pharmacol. 57:679-686 (2000).
Rudinger. "Characteristics of the amino acids as components of a peptide hormone sequence" in Peptide Hormones. J.A. Parsons (ed.) Baltimore, MD: Univ. Park Press, 1976; pp. 1-7.
Schnyder et al., "Targeting of skeletal muscle in vitro using biotinylated immunoliposomes" Biochem. J. 377:61-67 (2004).
Schuchman et al., "Human arylsulfatase B: MOPAC cloning nucleotide sequence of a full-length cDNA and regions of amino acid identity with aryisl1lfases A and C" Genomics 6(1):149-158 (1990).
Schwartz et al., "Preparation of Hydrazino-Modified Proteins and Their Use for the Synthesis of Tc-Protein Conjugates" Bioconjugate Chem. 2:333-336 (1991).
Schwarze et al., "In Vivo Protein Transduction: Delivery of a Biologically Active Protein into the Mouse" Science 285:1569-1572 (Sep. 1999).
Scott et al., "Human a-l-iduronidase: cDNA isolation and expression" Proc. Natl. Acad. Sci USA 88:9695-9699 (Nov. 1991).
Scott et al., "Structure and sequence of the human α-L-iduronidase gene" Genomics 13:1311-1313 (Aug. 1992).
Scott et al., "Molecular genetics of mucopolysaccharidosis type I: diagnostic clinical and biological. implications" Hum. Mutat. 6(4):288-302 (1995).
Scriver et al., The Metabolic and Molecular Bases of Inherited Disease. 8th edition, New York, 2001, cover page.
Sears et al., "Toward Automated Synthesis of Oligosaccharides and Glycoproteins" Science 291:2344-2350 (Mar. 2001).
Seeberger et al., "Automated synthesis of oligosaccharides as a basis for drug discovery" Nat. Rev. Drug Discov. 4(9):751-763 (2005).
Seeberger et al., "Synthesis and medical applications of oligosaccharides" Nature 446(7139):1046-1051 (Apr. 2007).
Seto et al., "A model for the acid sphingomyelinase phosphoesterase domain based on its remote strucutal homolog purple acid phosphatase" Protein Sci. 13:3172-3186 (2004).
Shen et al., "Conjugation of poly-L-iysine to albumin and horseradish peroxidase: A novel method of enhancing the cellular uptake of proteins" Proc. Natl. Acad. Sci USA 75:1872-1876 (1978).
Slodki, "Phosphate Linkages in Phosphomannans from Yeast" Biochim. Biophys. Acta 57:525-533 (1962).

Srivastava et al., "Synthesis of 6'-0-phosphorylated 0-a-D-mar. nopyranosyl-(1->3)-and -(1->6)-a-D mannoopyranosides" Carbohydr. Res. 161:324-329 (1987).
Srivastava et al., "Synthesis of Phosphorylated Pentasaccharides Found on Asparagine-Linked Carbohydrate Chains of Lysosomal Enzymes" J. Org. Chem. 52:2869-2875 (1987).
Srivastava et al., "Synthesis of Phosphorylated Trimannosides Corresponding to End Groups of the High-mannose Chains of Lysosomal Enzymes" Carbohydr. Res. 161:195-210 (1987).
Srivastava et al., "Synthesis of the 6- and 6'-Phosphates of 8-Methoxycarbonyloctyl 2-O-α-D-Mannopyranosyl-a-D-Mannopyranoside" Carbohydr. Res. 155:57-72 {1986).
Srivastava et al., "Synthesis of β-D-Mannopyranosides and Regioselective 0-Alkylation of Dibutyistannylene Complexes" Tetrahedron Letters 20(35):3269.-3272 (1979).
Sukegawa-Hayasaka et al., "Effect of Hunter Disease (Mucopolysaccharidosis Type II) Mutations on Molecular Phenotypes of Iduronate-2-Sulftase: Enzymatic Activity, Protein Processing and Structural Analysis" J. Inherit. Metab. Dis. 29(6):755-761 (2006).
Takahashi et al., "Acid Sphingomyelinase: Relation of Lysine Residue on the Ratio of Intracellular to Secreted Enzyme Activity" Tokohu J. Exp. Med. 206:333-340 (2005).
Tang et al., "Novel Approach to the Study of the Antigenicities and Receptor Functions of Carbohydrate Chains Glycoproteins" Biochem. Biophys. Res. Commun. 132(2):474-480 (1985).
Taylor et al., "Uptake and Processing of Glycoproteins by Rat Hepatic Mannose Receptor" Am. J. Physiol. Endocrinol, Metab. 252:E690-E698 (1987).
Tolvanen et al., "In vitro attachment of mono- and oligosaccharide to surface glycoconjugates of intact cells" J. Biol. Chem. 261(20):9546-9551 (Jul. 1986).
Tomoda et al., "Binding spec;ficity of D-mannose 6-phosphate receptor of rabbit alveolar macrophages" Carbohydr. Res. 213:3'?-46 (1991).
Tong et al, "Ligand Interactions of the Cation-independent Man nose 6-Phosphate Receptor" J. Biol. Chem. 264(14):7962-7969 (May 1989).
Torchilin, "Drug Targeting" Eur. J. Pharm. Sci. 11(Suppl. 2):S81-S91 (2000).
Townsend et al., "Analysis of Glycoprotein Oligosaccharides Using High-pH Anion Exchange Chromatography" Glycobiol. 1(2):139-147 (1991).
U.S. Appl. No. 16/439,665, filed Jul. 27, 2018, by Zhu, Y. (U.S. Patent Application is not submitted herewith pursuant to the waiver of 37 C.F.R. § 1.98(a)(2)(iii) issued by the Office on Sep. 21, 2004).
U.S. Office Action issued in U.S. Appl. No. 10/051,711, dated Sep. 30, 2003.
U.S. Office Action issued in U.S. Appl. No. 10/051,711, dated Apr. 16, 2004.
U.S. Office Action issued in U.S. Appl. No. 10/051,711, Notice of Allowance, dated Jun. 14, 2005.
U.S. Office Action issued in U.S. Appl. No. 10/051,711, dated Jan. 12, 2005.
U.S. Office Action issued in U.S. Appl. No. 10/943,893, dated Feb. 28, 2007.
U.S. Office.Action issued in U.S. Appl. No. 10/943,893, dated Sep. 20, 2007.
U.S. Office Action issued in U.S. Appl. No. 10/943,893, dated Jan. 30, 2008.
U.S. Office Action issued in U.S. Appl. No. 10/943,893, dated Sep. 25, 2008.
U.S. Office Action issued in U.S. Appl. No. 10/943,893, dated Dec. 17, 2008.
U.S. Office Action issued in U.S. Appl. No. 10/943,893: Notice of Allowance, dated Jun. 15, 2009.
U.S. Office Action issued in U.S. Appl. No. 10/943,893: Notice of Allowance, dated Sep. 25, 2009.
U.S. Office Action issued in U.S. Appl. No. 11/264,255, dated Oct. 12, 2007.
U.S. Office Action issued in U.S. Appl. No. 11/264,255, dated Jun. 25, 2008.
U.S. Office Action issued in U.S. Appl. No. 11/398,949, dated Jan. 31, 2007.

(56) References Cited

OTHER PUBLICATIONS

U.S. Office Action issued in U.S. Appl. No. 11/398,949: Notice of Allowance, dated Oct. 10, 2007.
U.S. Office Action issued in U.S. Appl. No. 11/970,907, U.S. Appl. No. Jun. 17, 2010.
U.S. Office Action issued in U.S. Appl. No. 11/970,907, dated Dec. 8, 2010.
U.S. Office Action issued in U.S. Appl. No. 11/970,907: Notice of Allowance, dated May 27, 2011.
U.S. Office Action issued in U.S. Appl. No. 11/970,907: Notice of Allowance, dated Oct. 26, 2011.
U.S. Office Action issued in U.S. Appl. No. 12/237,113, dated Nov. 19, 2009.
U.S. Office Action issued in U.S. Appl. No. 12/237,113: Notice of Allowance, dated May 3, 2010.
U.S. Office Action issued in U.S. Appl. No. 12/642,383, dated Mar. 13, 2012.
U.S. Office Action issued in U.S. Appl. No. 12/642,383: Notice of Allowance, dated Nov. 16, 2012.
Umapathysivam et al., "Determination of Acid α-Glucosidase Activity in Blood Spots as a Diagnostic Test for Pompe Disease" Clin. Chem. 47(8):1378-1383 (2001).
Valenzano et al., "Soluble Insulin-Like Growth factor II/Mannose 6-Phosphate Receptor Carries Multiple High Molecular Weight Forms of Insulin-like Growth Factor II in Fetal Bovine Serum" J. Biol. Chem. 270 16441-16448 (Jul. 1995).
Van Der Ploeg et al., "Intravenous Administration of Phosphorylated Acid a-Glucosidase Leads to Uptake of Enzyme in Heart and Skeletal Muscle of Mice" J. Clin. Invest. 87:513-518 (1991).
Van Diggelen et al., "A new fuorirnetric enzyme assay for the diagnosis of Niemann-Pick A/8 with specificity of natural sphingomyelinase substrate" J. Inherit. Metab. Dis. 28:733-741 (2005).
Van Hove et al., "High-Level Production of Recombinant Human Lysosornal Acid a-Glucosidase in Chinese Hamster Ovary Cells which Targets to Heart Muscle and Corrects Glycogen Accumulation in Fibroblasts from Patients with Pompe Disease" Proc Natl. Acad. Sci. USA 93:65-70 (Jan. 1996).
Varki et al., "Structural Studies of Phosphorylated High Mannose-type Oligosaccharides" J. Biol. Chem. 255:10847-10858 (1980).
Vilaseca et al., "Protein Conjugates of Defined Structure: Synthesis and Use of a New Carrier Molecule" Bioconj. Chem. 4:515-520 (1993).
Voznyi et al., "A fluorimetric enzyme assay for the diagnosis of MPS II (Hunter disease)" J. Inherit. Metab. Dis. 24:675-680 (2001).
Wadhwa et al., "Receptor Mediated Glycotargeting" J. Drug Targeting 11 (5):255-268 (2003).
Waller et al. (2001) "Sites and Mechanisms of Drug Action," Chapter 1 in Medical Pharmacology and Therapeutics, The British Library; pp. 13-16.
Wang et al., "Single-Chain Fv with manifold N-glycans as biofunctional scaffolds for immunomolecules" Protein Eng. 11(12):1277-1283 (1998).
Wang et al., "Addition of the keto functional group to the genetic code of *Escherichia coli*" PNAS 100:56-61 (2003).
Wender et al., "The design, synthesis, and evaluation of molecules that enable of enhance cellular uptake: Peptoid molecular transporters" PNAS 97(24):13003-13008 (2000).
Wieder et al., "Enzyme Therapy: II. Effect of Covalent Attachment of Polyethylene Glycol on Biochemical Parameters and Immunological Determinants of β-Glucosidase and α-Galactosidase" J. Appl. Biochem. 5:337-347(1983).
Wilchek et al., "Labeling Glycoconjugates with Hydrazide Reagents" Meth. Enzymol. 138:429-442 (1987).
Wilson et al., Hunter syndrome: Isolation of an iduronate-2-sulfatase cDNA clone and analysis of patient DNA Proc. Natl. Acad. Sci. USA 87.8031-8535 (Nov. 1990).
Wilson et al., "Sequence of the Human Iduronate 2-Sulfatase (IDS) Gene" Genomics 17:773-775 (1993).
Wu et al., "Targeting Hepatocytes for Drug and Gene Delivery: Emerging Novel Approaches and Applications" Frontiers in Bioscience 7:717-725 (Mar. 1, 2002).
Yamazaki et al., "Endogenous Lectins as Targets for Drug Delivery" Adv. Drug Deliv. Rev. 43:225-244 (2000).
Yamazaki et al., "Synthesis of α-D-Manp-(1→3)-β-D-GlcpNAc-(-1-4)-[α-D-Manp-(1-6)]-β-D-GlcpNAc-(1-4)-[α-L-Fucp-(1-6)]-D-GlcpNAc, a core glycohepatose of a 'bisected' complex-type glycan of glycoproteins" Carb. Res. 201:31-50 (1990).
Yoon et al. "Targeted Gene Correction of Episomal DNA in Mammalian Cells Mediated by a Chimeric RNA-DNA Oligonucleotide", Proc. Nati. Acad. Sci. USA 93:2071-2076, (Mar. 1996).
Yurkovetskiy et al., "Fully Degradable Hydrophilic Polyals for Protein Modification" Biomacromolecules 6:2648-2658 (2005).
Zalipsky et al., "Hydrazide Derivatives of Poly(ethylene glycol) and Their Bioconjugates" Poly(ethylene glycol) Chemistry and Biological Applications 680:318-341(1997).
Zara et al., "A Carbohydrate-Directed Heterobifunctional Cross-Linking Reagent for the Synthesis of immunoconjugates" Anal. Biochem. 194:156-162 (1991).
Zhang et al., "Linking Carbohydrates to Proteins Using N-(2,2-Dirnethoxyethyl)-6-hydroxy Hexanamide" Tetrahedron 54:11783-11792 (1998).
Zhao et al., "Purification and Characterization of Recombinant Human α-N-Acetylglucominidase Secreted by Chinese Hamster Ovary Cells" Prot. Expression Purif. 19:202-211 (2000).
Zhou et al., "Mannose 6-Phosphate Quantilation in Glycoproteins Using High-pH Anion-Exchange Chromatography with Pulsed Amperometric Detection" Anal. Biochem. 306:163-170 (2002).
Zhou et al., "Strategies for Neoglycan Conjugation to Human Acid α-Glucosidase" Bioconj. Chem. 22:741-751 (2011).
Zhu et al., "Glycoengineered Acid α-Glucosidase with Improved Efficacy at Correcting the Metabolic Aberrations and Motor Function Deficits in a Mouse Model of Pompe Disease" Mol. Ther. 17(6):954-963 (2009).
Zhu et al., "Carbohydrate-remodelled acid a-glucosidase with higher affinity for the cation-independent mannose 6-phosphate receptor demonstrates improved delivery to muscles of Pompe mice" Biochem J. 389: 619-628 (2005).
Zhu et al., "Conjugation of Mannose 6-Phosphate-containing Oligosaccharides to Acid a Glucosidase Improves the Clearance of Glycogen in Pompe Mice" J Biol. Chem. 279:50336-50341 (2004).

OLIGOSACCHARIDES COMPRISING AN AMINOOXY GROUP AND CONJUGATES THEREOF

This application is a continuation of U.S. patent application Ser. No. 15/280,864, filed Sep. 29, 2016, which is a continuation of U.S. patent application Ser. No. 14/272,960, filed May 8, 2014, which is a continuation of U.S. patent application Ser. No. 12/523,631, which adopts the international filing date of Jan. 18, 2008 (now U.S. Pat. No. 8,759,501), which is a national stage filing under 35 U.S.C. § 371 of International Application No. PCT/US08/51429, filed Jan. 18, 2008, and which claims the benefit of U.S. Provisional Application No. 60/885,471, filed Jan. 18, 2007, the disclosures of which are incorporated herein by reference in their entirety.

The invention relates generally to methods for the synthesis of oligosaccharides comprising an aminooxy group from oligosaccharides comprising a reactive group. In another embodiment, the invention further relates to oligosaccharides comprising an aminooxy group. The invention also relates to methods of conjugating oligosaccharides comprising an aminooxy group to proteins, including glycoproteins (such as, e.g., lysosomal enzymes), and to compositions of oligosaccharide-protein conjugates, including oligosaccharide-glycoprotein conjugates. Another embodiment of the invention relates to methods of treating lysosomal storage disorders using such oligosaccharide-lysosomal enzyme conjugates.

Lysosomal storage disorders (LSDs) are a class of rare metabolic disorders comprising over forty genetic diseases involving a deficiency in the activity of lysosomal hydrolases. A hallmark feature of LSDs is the abnormal accumulation of lysosomal metabolites, which leads to the formation of large numbers of distended lysosomes.

LSDs can be treated by administration of the active version of the enzyme deficient in the patient, a process termed enzyme replacement therapy (ERT). The administered replacement enzyme bearing a terminal mannose-6-phosphate (M6P) is taken up by target cells through cell-surface-associated cation-independent M6P receptor (CI-MPR)-mediated endocytosis, and directed to the lysosome.

In general, poorly phosphorylated replacement enzymes are not internalized by the M6P receptor on cell surfaces, and therefore cannot be directed to the lysosome where they function. Consequently, a low degree of mannose phosphorylation can have a significant and deleterious effect on the therapeutic efficacy of a replacement enzyme.

Methods thus have been developed for increasing the M6P content of replacement enzymes. U.S. Pat. No. 7,001,994, for example, describes a method for coupling oligosaccharides comprising M6P with glycoproteins. The oligosaccharides of the glycoproteins are first oxidized with periodate or galactose oxidase to result in the formation of carbonyl groups, which are then chemically conjugated with an oligosaccharide functionalized at the reducing end with a carbonyl-reactive group (such as, e.g., a hydrazine, hydrazide, aminooxy, thiosemicarbazide, semicarbazide, or amine group) to yield an oligosaccharide-glycoprotein conjugate.

A conjugate of the lysosomal enzyme acid α-glucosidase (GAA) with a a bis-M6P oligosaccharide was prepared by the above-described method, and found to be more effective in reducing skeletal and cardiac muscle glycogen than recombinant human GAA in a murine model of Pompe disease, an autosomal recessive muscular disease resulting from a metabolic deficiency of GAA, and characterized by the accumulation of lysosomal glycogen.

Aminooxy groups are particularly useful carbonyl-reactive groups for the conjugation reactions described above, as the resulting conjugates comprise a relatively stable oxime linkage. Therefore, there is a need for methods for the preparation of aminooxy functionalized oligosaccharides.

The present invention provides methods of preparing oligosaccharides comprising an aminooxy group. These methods are generally applicable to a broad range of protected and unprotected oligosaccharides, such as, e.g., branched and unbranched, and phosphorylated and unphosphorylated, oligosaccharides. In certain embodiments, the oligosaccharide may be a disaccharide, trisaccharide, tetrasaccharide, pentasaccharide, hexasaccharide, heptasaccharide, or greater. The oligosaccharide may, in certain embodiments, comprise at least one M6P residue. In some embodiments, the oligosaccharide may comprise at least 1, 2, 3, 4, 5, 6, or 7 terminal M6P residues.

The invention provides a method of preparing an oligosaccharide comprising an aminooxy group from an oligosaccharide comprising a reactive group. The method comprises:

(a) providing an oligosaccharide comprising a first reactive group;

(b) providing an aminooxy compound comprising an aminooxy group and a second reactive group; and (c) reacting the first reactive group of the oligosaccharide with the second reactive group of the aminooxy compound, thereby preparing the oligosaccharide comprising an aminooxy group.

The first and second reactive groups may be chosen from, e.g., hydrazine, hydrazide, thiosemicarbazide, semicarbazide, amine, carboxyl, activated ester, acyl halide, acyl azide, alkyl halide, anhydride, isothiocyanate, isocyanate, and sulfonyl halide groups.

In some embodiments, the aminooxy compound is chosen from compounds of Formula II:

Formula II wherein Y is the second reactive group, Z is chosen from alkyl, alkenyl, alkynyl, aryl, heteroaryl, and heterocyclyl, and P is chosen from amino protecting groups (such as, e.g., carbamate protecting groups). For example, in some embodiments, Y may be a carboxyl, activated ester, acyl halide (such as, e.g., an acyl fluoride or acyl chloride), acyl azide, alkyl halide, anhydride, isothiocyanate, isocyanate, or sulfonyl halide (such as, e.g., a sulfonyl chloride or sulfonyl bromide). In other embodiments, Y may be, e.g., a hydrazine, hydrazide, thiosemicarbazide, semicarbazide, or amine group.

In certain embodiments, the aminooxy compound of Formula II is chosen from compounds of Formula III:

Formula III wherein Y is the second reactive group, n is chosen from integers ranging from 1 to 10, and P is chosen from amino protecting groups.

In certain embodiments, the aminooxy compound comprises an amino protecting group, and the method further comprises a step (d), deprotecting the oligosaccharide comprising an aminooxy group.

The invention further provides an oligosaccharide comprising (1) an aminooxy group and (2) mannose-6-phosphate. In some embodiments, that oligosaccharide is prepared by the methods described above. For example, in some embodiments, the invention provides an oligosaccharide comprising an aminooxy group of Formula IV:

In another embodiment, the invention provides methods of coupling an oligosaccharide to a protein. In one embodiment, the method comprises:
(a) providing an oligosaccharide comprising an aminooxy group;
(b) providing a protein having at least one carbonyl group; and
(c) reacting the aminooxy group of the oligosaccharide with the at least one carbonyl group of the protein, thereby coupling the oligosaccharide to the protein.

Formula IV

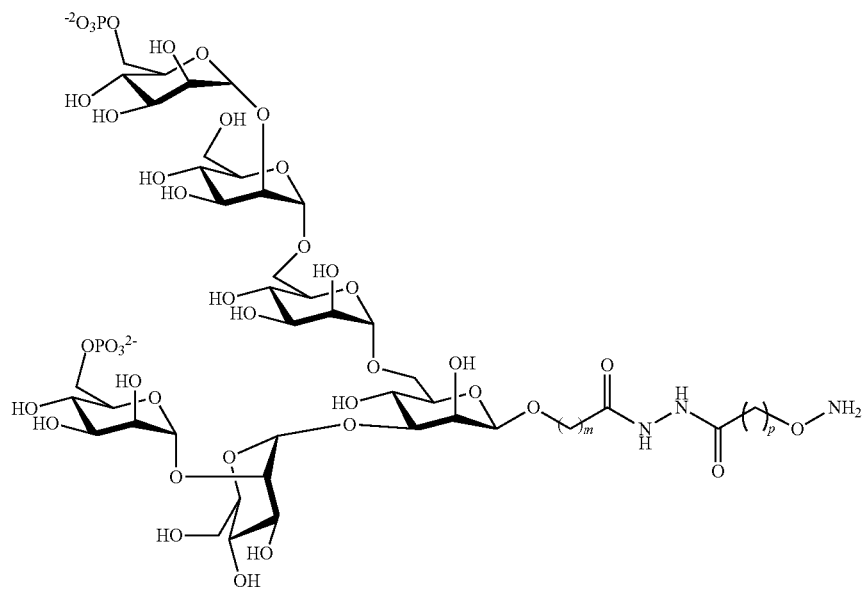

wherein m and p are independently chosen from integers ranging from 1 to 10.

In another embodiment, the invention provides an oligosaccharide of Formula V:

Formula V

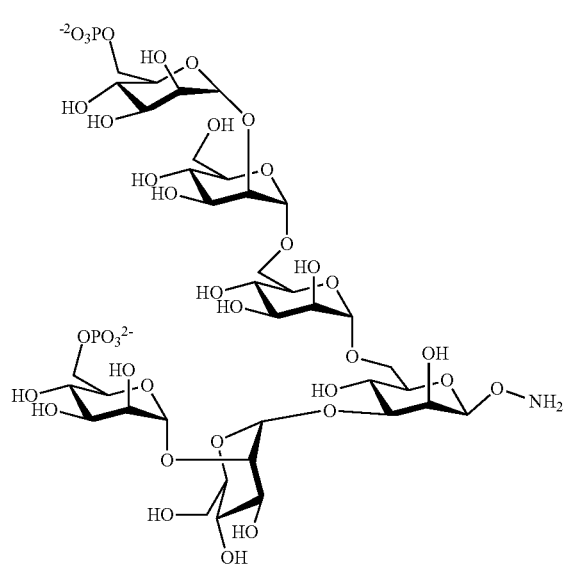

In other embodiments, the invention further provides an oligosaccharide-protein conjugate comprising (1) a protein, (2) an oligosaccharide, and (3) an oxime group connecting the protein and the oligosaccharide. For example, in some embodiments, the invention provides an oligosaccharide-protein conjugate prepared by the methods disclosed above. In certain embodiments, the oligosaccharide-protein conjugate is an oligosaccharide-glycoprotein conjugate. In certain embodiments, the oligosaccharide-glycoprotein conjugate is the conjugate of an oligosaccharide comprising at least one M6P and of a lysosomal enzyme such as, e.g., a lysosomal hydrolase. In some embodiments, the invention provides pharmaceutical compositions comprising an oligosaccharide-protein conjugate of the invention.

Another embodiment of the invention provides methods of treating a lysosomal storage disorder such as, e.g., those disclosed in Table 1. In some embodiments, the methods comprise administering to a mammal an oligosaccharide-glycoprotein conjugate of the invention, wherein the oligosaccharide comprises at least one M6P and the glycoprotein is a lysosomal hydrolase. This disclosure further provides the use of a conjugate of the invention for treating a lysosomal storage disorder in a subject in need thereof, and in the manufacture of a medicament for treating a lysosomal storage disorder.

BRIEF DESCRIPTION OF THE FIGURES

FIG. 2 depicts a series of gel chromatographs of intermediates in the synthetic scheme described in FIG. 1.

I. PREPARATION OF AN OLIGOSACCHARIDE COMPRISING AN AMINOOXY GROUP

A. Oligosaccharide Comprising a Reactive Group

Figure 1:
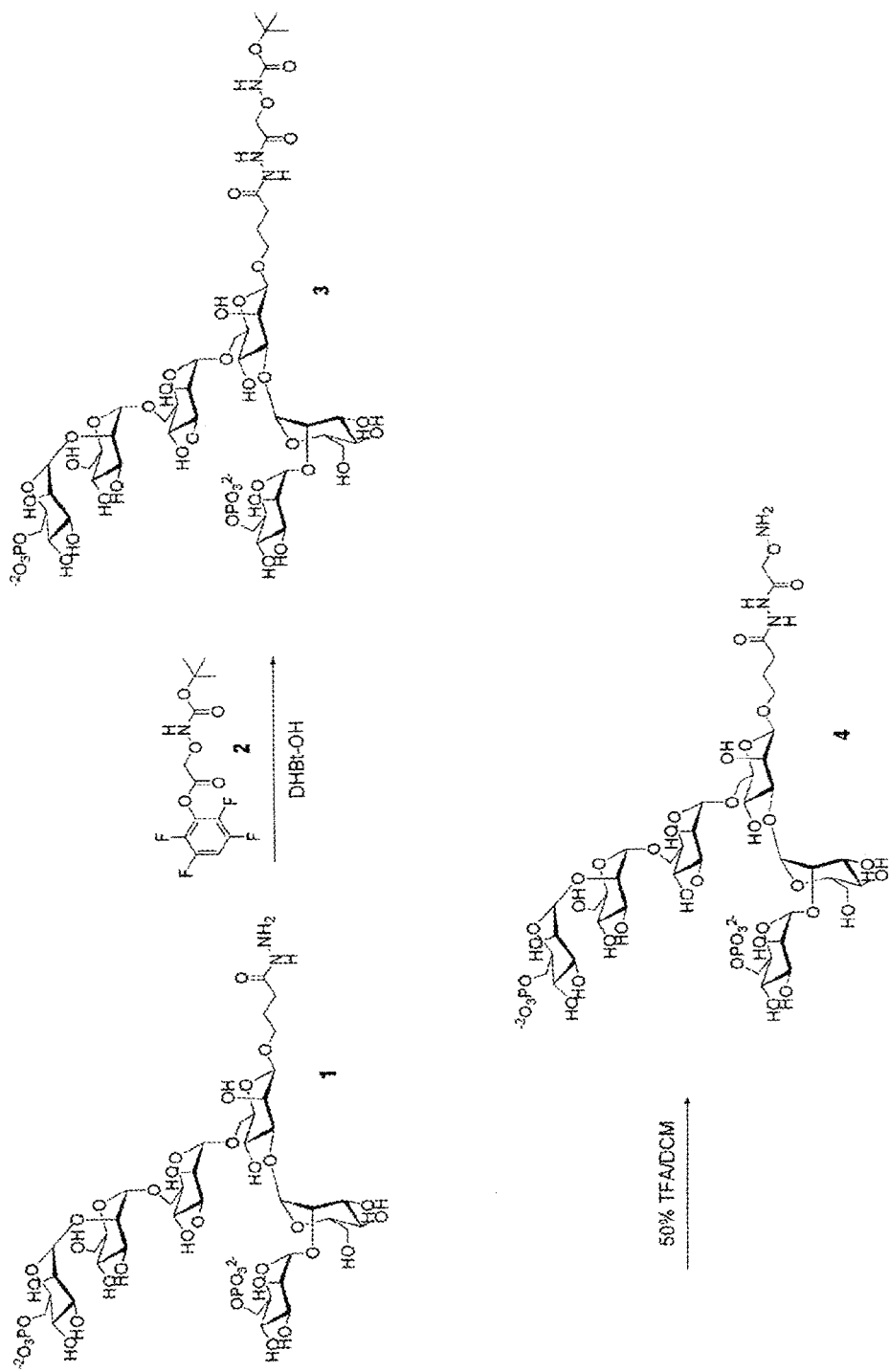
FIG. 1 is a reaction scheme depicting an illustrative embodiment of the methods of the invention. Oligosaccharide 1, having a first reactive group (a hydrazide group), is reacted with aminooxy compound 2 in presence of the catalyst 3-hydroxy-1,2,3-benzotriazin-4(3H)-one (DHBt-OH), to yield oligosaccharide 3. The tert-butyloxycarbonyl (t-Boc) amino protecting group of oligosaccharide 3 is then removed with 50% trifluoroacetic acid/dichloromethane (TFA/DCM) to yield oligosaccharide 4.

The methods of the invention are applicable to a broad range of oligosaccharides comprising a reactive group. As used herein, an oligosaccharide refers to a disaccharide, trisaccharide, tetrasaccharide, pentasaccharide, hexasaccharide, heptasaccharide, or larger oligosaccharide (such as, e.g., an oligosaccharide comprising 2-50, 2-10, 8-25, or 8-50 saccharide units). Accordingly, in various embodiments, an oligosaccharide may be, e.g., a disaccharide, trisaccharide, tetrasaccharide, a pentasaccharide, a hexasaccharide, a heptasaccharide, or a larger oligosaccharide. An oligosaccharide may be mono-, bi-, tri-, tetra-, or penta-antennary in structure. An oligosaccharide may comprise 0, 1, 2, 3, 4, or more branch points.

The reactive group on the oligosaccharide, also referred to as a first reactive group, may be, in some embodiments, e.g., a hydrazine group, hydrazide group, semicarbazide group, thiosemicarbazide, or amine group. In some embodiments, the first reactive group may be, e.g., a carboxyl, ester (such as, e.g., an activated ester), acyl halide (such as, e.g., acyl fluoride or acyl chloride), acyl azide, alkyl halide, anhydride, isothiocyanate, isocyanate, or sulfonyl halide (such as, e.g., sulfonyl chloride or sulfonyl bromide) group.

The first reactive group may be connected to the reducing end of the oligosaccharide or may be located anywhere in the oligosaccharide. The first reactive group may, in certain embodiments, be connected through one or more linkers to the oligosaccharide. A linker, as used herein, may be chosen from, e.g., a combination of optionally substituted alkyl, alkenyl, alkynyl, aryl, heteroaryl, heterocyclyl, acyloxy, alkoxy, aryloxy, and heterocyclyloxy groups. A linker may be interrupted or terminated by one or more heteroatoms such as, e.g., nitrogen, sulfur, and oxygen. For example, a linker, in some embodiments, may comprise one or more ether, ester, or amide group.

Any chemical group of the linker (such as, e.g., alkyl, alkenyl, alkynyl, aryl, heteroaryl, heterocyclyl, acyloxy, alkoxy, aryloxy, and heterocyclyloxy) may be substituted or unsubstituted, unless otherwise stated. Substituents may be chosen from, e.g., acyl, acylamino, acyloxy, alkenyl, alkoxy, alkyl, alkynyl, amido, amino, aryl, aryloxy, azido, carbamoyl, carboalkoxy, carboxy, cyano, cycloalkyl, formyl, guanidino, halo, heteroaryl, heterocyclyl, hydroxy, iminoamino, nitro, oxo, phosphonamino, sulfinyl, sulfonamino, sulfonate, sulfonyl, thio, thioacylamino, thioureido, and ureido. The substituents may themselves be substituted or unsubstituted, and may be interrupted or terminated by one or more heteroatoms such as, e.g., nitrogen, sulfur, and oxygen.

In certain embodiments, an oligosaccharide may comprise at least one protecting group. The term "protecting group" refers to any substituent that may be used to prevent a functional group (such as, e.g., an amine group, a carboxyl group, a hydroxyl group, a hydrazine group, a hydrazide group, a semicarbazide group, or a thiosemicarbazide group) on a molecule from undergoing a chemical reaction while chemical change occurs elsewhere in the molecule. A protecting group can be removed under the appropriate chemical conditions. Numerous protecting groups are known to those skilled in the art, and examples of protecting groups, methods for their addition, and methods for their removal can be found in, e.g., Greene et al., *Protective Groups in Organic Synthesis*, $3^{rd}$ ed., John Wiley and Sons: New York, 1999 and Kocienski, *Protecting Groups*, $3^{rd}$ ed., Georg Thieme Verlag: Stuttgard, Germany, 2005, the disclosures of which are herein incorporated by reference. In certain embodiments, the oligosaccharide may comprise at least one protecting group chosen from hydroxyl protecting groups, carboxyl protecting groups, and amino protecting groups. In other embodiments, an oligosaccharide may be "unprotected," and may not comprise any protecting groups.

An oligosaccharide may be isolated from a natural source or may be prepared by chemical or enzymatic synthesis. An oligosaccharide isolated from a natural source may be homogeneous or may be a heterogeneous mixture of related oligosaccharides. In some embodiments, an oligosaccharide may be prepared by chemical or enzymatic modification of an oligosaccharide isolated from a natural source ("semi-synthesis"). In some embodiments, the oligosaccharide may be a synthetic oligosaccharide having the chemical structure of a naturally occurring oligosaccharide.

In some embodiments, an oligosaccharide may comprise a monosaccharide that is recognized by a particular receptor. The monosaccharide recognized by a particular receptor may be chosen from, e.g., galactose, GalNAc, mannose, M6P, glucose, GlcNAc, sialic acid, or sulfated sialic acid residue. An oligosaccharide may, in certain embodiments, comprise at least one M6P residue, such as, e.g., 1, 2, 3, 4, 5, 6, 7, 8, 9, or 10 M6P residues.

The monosaccharide recognized by a particular receptor may be, in some embodiments, a penultimate monosaccharide or a terminal monosaccharide. In some embodiments, the monosaccharide recognized by a particular receptor may be a terminal galactose, mannose, M6P, glucose, GlcNAc, or sialic acid residue. An oligosaccharide may, in some embodiments, contain at least 1, 2, 3, 4, 5, 6, 7 terminal M6P residues.

In certain embodiments, the oligosaccharide comprising a reactive group may be an M6P-containing hexasaccharide of Formula Ia:

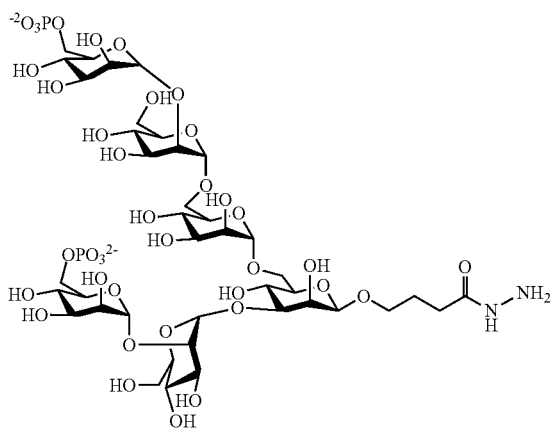

Formula Ia

The oligosaccharide of Formula Ia can be described as butyrylhydrazine-4-yl 6-O-phosphono-α-D-mannopyranosyl-(1→2)-α-D-mannopyranosyl-(1→6)-α-D-mannopyranosyl-(1→6)-[6-O-phosphono-α-D-mannopyranosyl-(1→2)-α-D-mannopyranosyl-(1→3)]-β-D-mannopyranoside.

In certain embodiments, the oligosaccharide comprising a reactive group may be an M6P-containing hexasaccharide of Formula Ib:

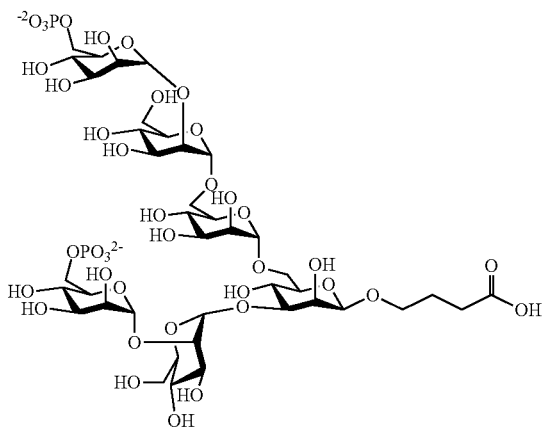

Formula Ib

B. Aminooxy Compound

As used herein, an aminooxy compound may be any compound comprising an aminooxy group and a second reactive group, wherein the second reactive group may react with a first reactive group on an oligosaccharide to form a covalent bond. For example, in some embodiments, the second reactive group may be a carboxyl, ester (such as, e.g., an activated ester), acyl halide (such as, e.g., an acyl fluoride or acyl chloride), acyl azide, anhydride, isothiocyanate, isocyanate, or sulfonyl halide (such as, e.g., a sulfonyl chloride or sulfonyl bromide) group. In other embodiments, the second reactive group may be, e.g., a hydrazine group, hydrazide group, semicarbazide group, thiosemicarbazide, or amine group.

In certain embodiments, the nitrogen of the aminooxy group of the aminooxy compound is protected with an amino protecting group. Numerous amino protecting groups are known to those skilled in the art, and examples of amino protecting groups, methods for their addition, and methods for their removal can be found in pp. 494-653 of Greene et al., *Protective Groups in Organic Synthesis*, 3$^{rd}$ ed., John Wiley and Sons: New York, 1999; Chapter 8 of Kocienski, *Protecting Groups*, 3$^{rd}$ ed., Georg Thieme Verlag: Stuttgard, Germany, 2005; Bodanszky, *Principles of Peptide Synthesis*, Springer Verlag: New York, 1993; Lloyd-Williams et al., *Chemical Approaches to the Synthesis of Peptides and Proteins*, CRC Press: Boca Raton, Fla., 1997; and Stewart et al., *Solid Phase Peptide Synthesis*, 2nd ed., Pierce Chemical Co.: Rockford, Ill., 1984, the inventions of which are incorporated herein by reference.

In some embodiments, the aminooxy compound is chosen from compounds of Formula II:

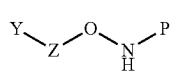

Formula II wherein Y is the second reactive group, Z is chosen from alkyl, alkenyl, alkynyl, heteroaryl, aryl, and heterocyclyl, and P is chosen from amino protecting groups.

As used herein, any chemical group on the aminooxy compound (such as, e.g., alkyl, alkenyl, alkynyl, aryl, heteroaryl, heterocyclyl, acyloxy, alkoxy, aryloxy, and heterocyclyloxy) may be substituted or unsubstituted, and may be interrupted by one or more chemical groups, unless otherwise stated. Substituents and interrupting chemical groups may be chosen from, e.g., acyl, acylamino, acyloxy, alkenyl, alkoxy, alkyl, alkynyl, amido, amino, aryl, aryloxy, azido, carbamoyl, carboalkoxy, carboxy, cyano, cycloalkyl, formyl, guanidino, halo, heteroaryl, heterocyclyl, hydroxy, iminoamino, nitro, oxo, phosphonamino, sulfinyl, sulfonamino, sulfonate, sulfonyl, thio, thioacylamino, thioureido, and ureido. The substituents may themselves be substituted or unsubstituted, and may be interrupted or terminated by one or more heteroatoms such as, e.g., nitrogen, sulfur, and oxygen.

In certain embodiments, Y may be chosen from, for example:

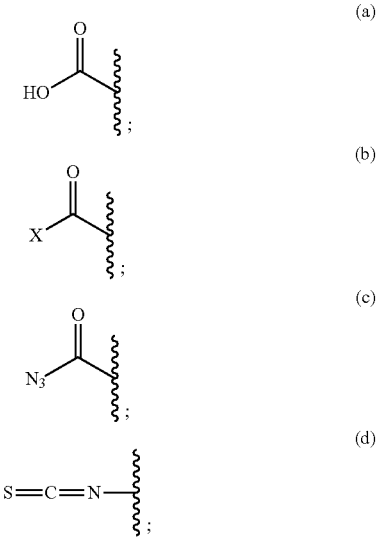

(e)
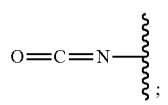

(f)
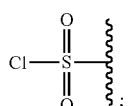

(g)
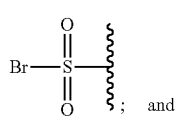; and (h)
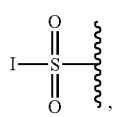, wherein X is chosen from halogens, azide, acyloxy, alkoxy, aryloxy, heteroaryloxy, and heterocyclyloxy.

In certain embodiments, the aminooxy compound is an activated ester. As used herein, an activated ester is an ester that reacts to form an amide bond under mild conditions. In general, an activated ester is an ester of a relatively acidic alcohol. In certain embodiments, the aminooxy compound of Formula II is an activated ester of formula

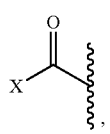, and X is chosen from alkoxy, aryloxy, heteroaryloxy, and heterocyclyloxy. For example, X may be chosen from:

(a)
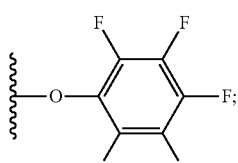

(b)
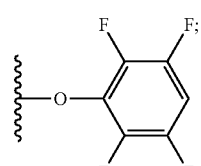

(c)
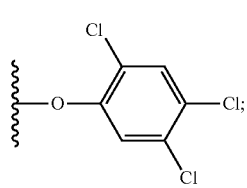

(d)
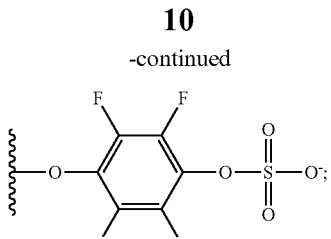

(e)
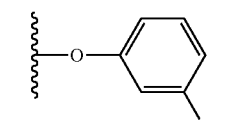

(f)
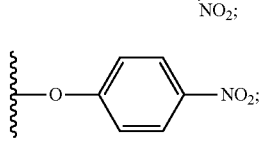

(g)
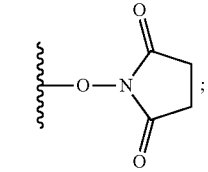

(h)
—OCF$_2$CF$_3$;

(i)
—SCH$_2$CH$_3$;

(j)
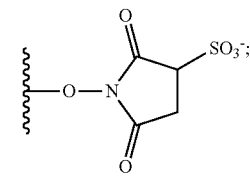

(k)
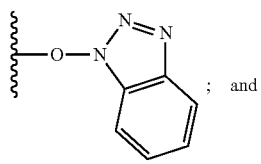; and (l)
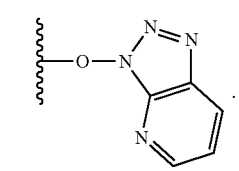.

In other embodiments, Y is chosen from, e.g., hydrazide, hydrazine, thiosemicarbazide, semicarbazide, and amine groups.

In some embodiments, Z may comprise, for example, a carbonyl, ether, ester, or amide group. In some embodiments, Z may be, for example, alkyl interrupted by one or more heteroatoms, such as an oligoethyleneglycol. For example, Z may be monoethyleneglycol, diethyleneglycol, triethyleneglycol, tetraethyleneglycol, or larger oligoethyleneglycol.

In some embodiments, Z may be, for example, alkyl substituted with oxo and interrupted by one or more heteroatoms, such as an oligopeptide. For example, the oligopeptide may comprise one, two, three, four, five, six, or more component amino acids. The amino acids may be, for example, α-amino acids, β-amino acids, γ-amino acids, δ-amino acids, and ω-amino acids. An amino acid may have R or S chirality at any chiral atom. An amino acid may be chosen from, e.g., alanine, β-alanine, α-aminoadipic acid, 2-aminobutanoic acid, 4-aminobutanoic acid, 1-aminocyclopentanecarboxylic acid, 6-aminohexanoic acid, 2-aminoheptanedioic acid, 7-aminoheptanoic acid, 2-aminoisobutyric acid, aminomethylpyrrole carboxylic acid, 8-amino-3,6-dioxa-octanoic acid, aminopiperidinecarboxylic acid, 3-amino-propionic acid, aminoserine, aminotetrahydropyran-4-carboxylic acid, arginine, asparagine, aspartic acid, azetidine carboxylic acid, benzothiazolylalanine, butylglycine, carnitine, 4-chlorophenylalanine, citrulline, cyclohexylalanine, cyclohexylstatine, cysteine, 2,4-diaminobutanoic acid, 2,3-diaminopropionic acid, dihydroxyphenylalanine, dimethylthiazolidine carboxylic acid, glutamic acid, glutamine, glycine, histidine, homoserine, hydroxyproline, isoleucine, isonipecotic acid, leucine, lysine, methanoproline, methionine, norleucine, norvaline, ornithine, p-aminobenzoic acid, penicillamine, phenylalanine, phenyiglycine, piperidinylalanine, piperidinylglycine, proline, pyrrolidinylalanine, sarcosine, selenocysteine, serine, statine, tetrahydropyranglycine, thienylalanine, threonine, tryptophan, tyrosine, valine, allo-isoleucine, alto-threonine, 2,6-diamino-4-hexanoic acid, 2,6-diaminopimelic acid, 2,3-diaminopropionic acid, dicarboxidine, homoarginine, homocitrulline, homocysteine, homocystine, homophenylalanine, homoproline, and 4-hydrazinobenzoic acid.

P may be chosen from amino protecting groups known to those of skill in the art. In some embodiments, P may be a carbamate protecting group, such as, e.g., a (9-fluorenylmethyl)carbamate (Fmoc), (tert-butyloxy)carbamate (t-Boc), (trichloroethyl)carbamate (Troc), or allylcarbamate (Alloc) protecting group. In other embodiments, P may be a non-carbamate protecting group, such as, e.g., an amide protecting group such as a phthalimide or a trifluoroacetamide protecting group.

In some embodiments, the aminooxy compound of Formula II is chosen from compounds of Formula III:

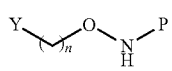

Formula III wherein Y and P are as disclosed above, and n is chosen from integers ranging from 1 to 10.

In certain embodiments, n may be chosen from integers from the following ranges: 1-4, 2-6, 2-8, 3-6, and 4-10. In illustrative embodiments, n is 1.

In one illustrative embodiment, the aminooxy compound is t-Boc-aminooxy acetic acid tetrafluorophenyl ester, the structure of which is depicted below.

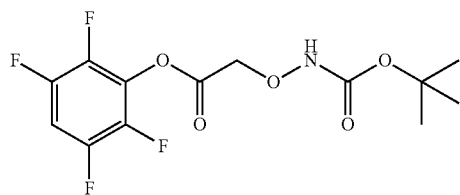 [SMILES: CC(C)(C)OC(=O)NOCC(=O)Oc1c(F)c(F)cc(F)c1F]

In another illustrative embodiment, the aminooxy compound has the structure depicted below.

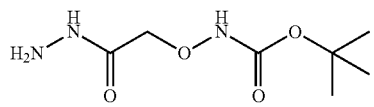

C. Methods of Preparing an Oligosaccharide Comprising an Aminooxy Group

In another embodiment, the invention provides a method of preparing an oligosaccharide comprising an aminooxy group from an oligosaccharide comprising a reactive group. The method comprises:
 (a) providing an oligosaccharide comprising a first reactive group;
 (b) providing an aminooxy compound comprising a second reactive group; and
 (c) reacting the first reactive group of the oligosaccharide with
  the second reactive group of the aminooxy compound, thereby preparing the oligosaccharide comprising an aminooxy group.

The oligosaccharide comprising a first reactive compound may be, e.g., any oligosaccharide comprising a reactive group as described supra. In illustrative embodiments, the oligosaccharide comprising a first reactive group is an oligosaccharide of Formula Ia or an oligosaccharide of Formula Ib. The aminooxy compound comprising a second reactive group may be any aminooxy compound comprising a reactive group, as described supra.

The terms "first reactive group" and "second reactive group," as used herein, do not denote any particular experimental sequence. I.e., step (c), reacting the first reactive group of the oligosaccharide with the second reactive group of the aminooxy compound, may be accomplished by any order of addition of the reactants. For example, the oligosaccharide comprising a first reactive group may be added to the aminooxy compound comprising the second reactive group, or vice versa. In another example, both the oligosaccharide and the aminooxy compound may be added simultaneously to a reaction vessel.

Step (c) may occur under any suitable conditions (e.g., solvent and temperature) known to those of ordinary skill in the art. In certain embodiments, one or more additional reagents, such as, e.g., coupling reagents and catalysts, may be present during step (c). A coupling reagent, as used herein, is a reagent that may be used to form a covalent bond between the first reactive group and the second reactive group.

In some embodiments, such as, e.g., when the first or second reactive group is a carboxyl group, the reaction conditions may comprise a coupling reagent. Coupling reagents may be chosen from, e.g., phosphonium coupling reagents such as, e.g., BOP (benzotriazole-1-yl-oxy-tris-(dimethylamino)-phosphonium hexafluorophosphate), PyBOP® (benzotriazole-1-yl-oxy-tris-pyrrolidino-phosphonium hexafluorophosphate), and PyBroP® (bromo-tris-pyrrolidino-phosphonium hexafluorophosphate), and from aminium (uronium) coupling reagents such as, e.g., HBTU (2-(1H-benzotriazole-1-yl)-1,1,3,3-tetramethyluronium hexafluorophosphate), HATU (2-(7-Aza-1H-benzotriazole-1-yl)-1,1,3,3-tetramethyluronium hexafluorophosphate), TBTU (2-(1H-Benzotriazole-1-yl)-1,1,3,3-tetramethyluronium tetrafluoroborate). Coupling reagents may also be chosen from, e.g., carbodiimide coupling reagents such as, e.g., DIC (1,3-diisopropylcarbodiimide), CDI (1,1' carbonyl diimidazole), and EDC (1-ethyl-3-(3-dimethylaminopropyl)-carbodiimide). For example, in some illustrative embodiments, the coupling reagent is EDC. In certain embodiments, the reaction conditions comprise both a coupling reagent and a catalyst.

The reaction conditions may, in certain embodiments, comprise a catalyst. The catalyst may be chosen from any suitable catalyst known to those of skill in the art, such as, e.g., DHBt-OH (3-hydroxy-1,2,3-benzotriazin-4(3H)-one), HOBt (N-hydroxybenzotriazole), DMAP (4-dimethylaminopyridine), NHS (N-hydroxysuccinimide), N-hydroxysulfosuccinimide, HONB (N-hydroxy-5-norbornene-endo-2,3-dicarboximide), or a tetrabutylammonium salt such as, e.g., TBAI (tetrabutylammonium iodide). In some illustrative embodiments, the reaction conditions comprise the catalyst DHBt-OH or the catalyst NHS.

In some embodiments, step (c), reacting the first reactive group of the oligosaccharide with the second reactive group of the aminooxy compound results in the formation of an amide bond. Conditions suitable for the formation of an amide bond are well known to those of ordinary skill in the art, and are described in, e.g., Chan et al., eds., *Fmoc Solid Phase Peptide Synthesis: A Practical Approach*, Oxford University Press: New York, 2000; Bodanszky, *Principles of Peptide Synthesis*, Springer Verlag: New York, 1993; Lloyd-Williams et al., *Chemical Approaches to the Synthesis of Peptides and Proteins*, CRC Press: Boca Raton, Fla., 1997; and the Novabiochem® (San Diego, Calif.) Catalog.

In certain embodiments, the aminooxy compound comprises an amino protecting group, and the method comprises a further step (d), deprotecting the oligosaccharide comprising an aminooxy group to remove the amino protecting group. Deprotection may occur under any suitable conditions known to those of skill in the art, such as, e.g., those taught in pp. 494-653 of Greene et al., *Protective Groups in Organic Synthesis*, 3$^{rd}$ ed., John Wiley and Sons: New York, 1999 and Kocienski, *Protecting Groups*, 3$^{rd}$ ed., Georg Thieme Verlag: Stuttgard, Germany, 2005, the inventions of which are incorporated herein by reference.

An illustrative embodiment of the method of the invention provides a method of preparing an M6P-containing oligosaccharide comprising an aminooxy group. The method comprises:

(a) providing an oligosaccharide comprising a first reactive group, wherein the oligosaccharide is

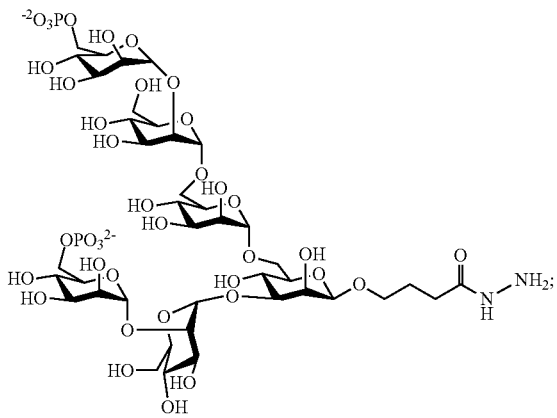

(b) providing an aminooxy compound comprising a second reactive group, wherein the aminooxy compound is chosen from compounds of Formula III:

Formula III wherein n is chosen from integers ranging from 1 to 10, P is chosen from amino protecting groups, and Y is a second reactive group; and (c) reacting the first reactive group of the oligosaccharide with the second reactive group of the aminooxy compound, thereby preparing the oligosaccharide comprising an aminooxy group.

In certain embodiments, Y in Formula III is

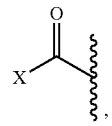

where X is chosen from hydroxy, aryloxy, heteroaryloxy, and heterocyclyloxy. For example, in certain illustrative embodiments, X is

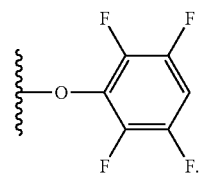 [SMILES: *Oc1c(F)c(F)cc(F)c1F]

15

In illustrative embodiments, the aminooxy compound is

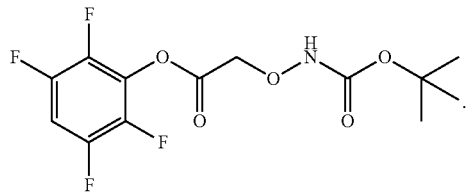 [SMILES: CC(C)(C)OC(=O)NOCC(=O)Oc1c(F)c(F)cc(F)c1F]

In certain embodiments, the first reactive group of the oligosaccharide may be reacted with the second reactive group of the aminooxy compound in the presence of a coupling agent, such as, e.g., EDC, and/or a catalyst, such as, e.g., DHBt-OH.

Another illustrative embodiment of the method of the invention comprises:

(a) providing an oligosaccharide comprising a first reactive group, wherein the oligosaccharide is

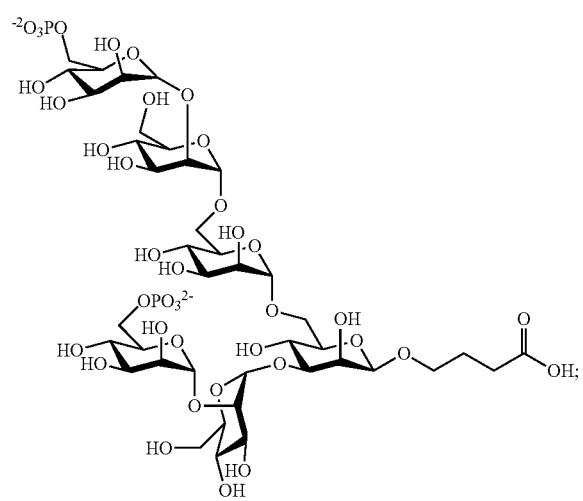

(b) providing an aminooxy compound comprising a second reactive group, wherein the aminooxy compound is chosen from compounds of Formula III:

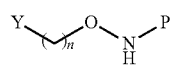

Formula III wherein n is chosen from integers ranging from 1 to 10, P is chosen from amino protecting groups, and Y is a second reactive group; and

16

(c) reacting the first reactive group of the oligosaccharide with the second reactive group of the aminooxy compound, thereby preparing the oligosaccharide comprising an aminooxy group.

In certain embodiments, Y in Formula III is a hydrazine, hydrazide, aminooxy, thiosemicarbazide, semicarbazide, or amine group. In certain embodiments, Y in Formula III is

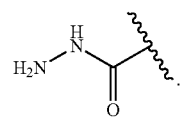

In illustrative embodiments, the aminooxy compound is

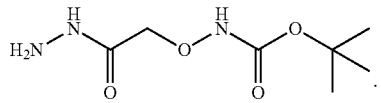

In certain embodiments, the first reactive group of the oligosaccharide may be reacted with the second reactive group of the aminooxy compound in the presence of a coupling agent, such as, e.g., EDC, and/or a catalyst, such as, e.g., NHS.

II. OLIGOSACCHARIDES COMPRISING AN AMINOOXY GROUP

The present invention also provides oligosaccharides comprising an aminooxy group. In some embodiments, the invention provides oligosaccharides comprising an aminooxy group prepared by the methods disclosed above. The oligosaccharide comprising an aminooxy group may comprise, for example, at least 2, 3, 4, 5, 6, or more monosaccharides, including, e.g., at least one galactose, GalNAc, mannose, M6P, glucose, GlcNAc, sialic acid, or sulfated sialic acid residue. Such an oligosaccharide may be mono-, bi-, tri-, tetra-, or penta-antennary in structure, and may contain 0, 1, 2, 3, 4, or more branch points.

In some embodiments, the present invention provides an oligosaccharide comprising (1) an aminooxy group and (2) mannose-6-phosphate. The oligosaccharide comprising an aminooxy group may, in some embodiments, comprise, e.g., 1, 2, 3, 4, 5, 6, 7, 8, 9, or 10 M6P residues. In some embodiments, the oligosaccharide comprising an aminooxy group may comprise at least 1, 2, 3, 4, or more terminal or penultimate M6P residues.

The oligosaccharides comprising an aminooxy group are, in certain embodiments, chosen from oligosaccharides of Formula IV:

Formula IV

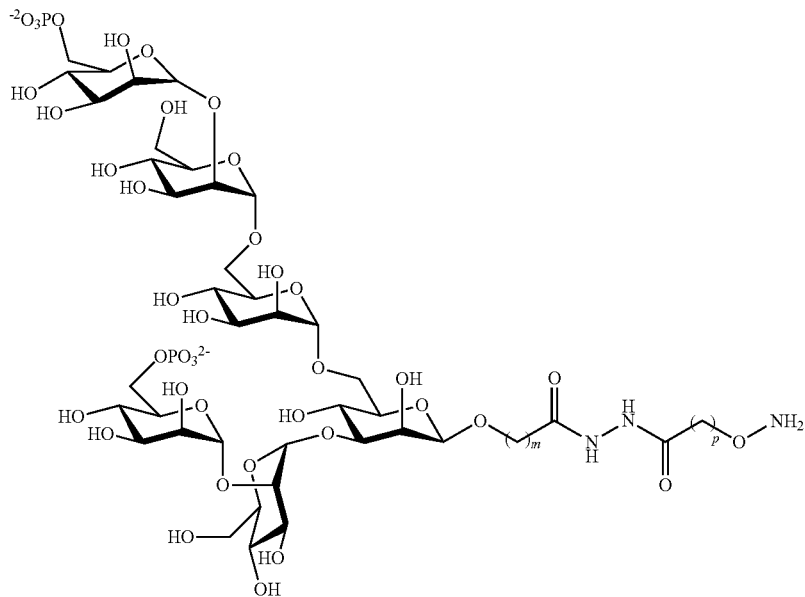

wherein m and p are independently chosen from integers ranging from 1 to 10. For example, in certain embodiments, m and p may be independently chosen from integers selected from the following ranges: 1-4, 2-6, 2-8, 3-6, and 4-10. In illustrative embodiments, m is 3 and p is 1.

In other embodiments, the aminooxy group is directly linked to the reducing end of the oligosaccharide. For example, in some embodiments, the oligosaccharide comprising an aminooxy group may be an oligosaccharide of Formula V:

Formula V

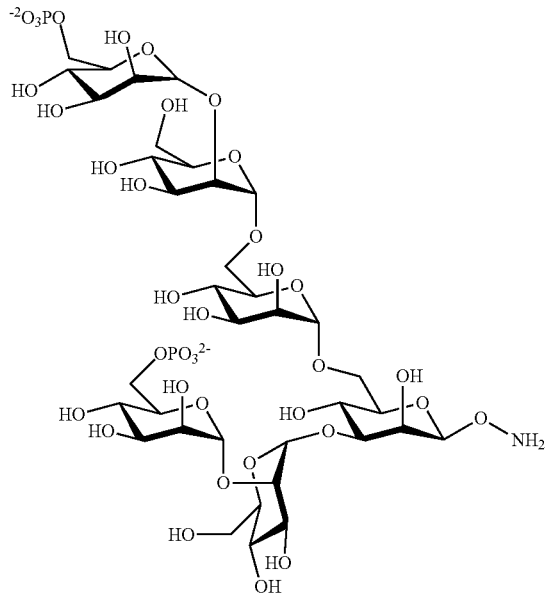

III. CONJUGATION OF AN OLIGOSACCHARIDE COMPRISING AN AMINOOXY GROUP WITH A PROTEIN

A. Oligosaccharide

The oligosaccharide to be conjugated with a protein may be chosen from any oligosaccharide comprising a reactive group, as discussed supra, and from any oligosaccharide comprising an aminooxy group, as discussed supra. For example, in some embodiments, the oligosaccharide to be conjugated may be an oligosaccharide of Formula Ia, Formula Ib, Formula IV or Formula V.

B. Protein

The conjugation methods described herein are broadly applicable to any pure protein, partially purified protein, or fragment thereof, having at least one carbonyl group (where a carbonyl group is a ketone or an aldehyde), including isolated proteins and recombinantly or synthetically produced proteins. The terms "pure," "purified," and "isolated" refer to a molecule that is substantially free of its natural environment. For instance, a pure protein is substantially free of cellular material and/or other proteins from the cell or tissue source from which it is derived. The term refers to preparations that are, for example, at least 70% to 80%, 80% to 90%, 90 to 95%; or at least 95%, 96%, 97%, 98%, 99%, or 100% (w/w) pure.

In other embodiments, the protein may be an enzyme that has optimal activity, as measured by an activity assay, at a pH ranging from 1-7, such as, e.g., 1-3, 2-5, 3-6, 4-5, 5-6, or 4-6. For example, the enzyme may have a pH optimum at a pH ranging from 4-6.

In some embodiments, the protein may be an enzyme that has an isoelectric point (pI), ranging from 1 to 8, such as, e.g., from 1-3, 2-5, 3-8, 4-5, 5-6, 4-6, 5-8, 6-8, or 7-8. The pI of a protein may be may be measured using, e.g., isoelectric focusing gel electrophoresis.

In some embodiments, the protein containing a carbonyl group is obtained by the use of an expression system having an expanded genetic code, as described in, e.g., Wang et al.,

*Proc. Natl. Acad. Sci. USA* 100:56-61 (2003). In such a case, the carbonyl group may be located on amino acid side chain, as translated.

In certain embodiments, the protein having at least one carbonyl group is a protein having at least one oligosaccharide (i.e., a glycoprotein). For example, a glycoprotein having at least one carbonyl group may be obtained by oxidation of that glycoprotein by any means known to those of skill in the art. In some embodiments, e.g., a glycoprotein having at least one carbonyl group may be obtained by oxidation of that glycoprotein with periodate (e.g., sodium periodate) or with galactose oxidase. In such a case, the carbonyl group may be located at a protein glycosylation site.

In certain embodiments, the protein having at least one carbonyl group is a glycoprotein, such as a therapeutic glycoprotein. A therapeutic glycoprotein may be targeted to the lysosome by conjugation with an oligosaccharide comprising mannose-6-phosphate. For example, the glycoprotein may be a lysosomal enzyme, including an ERT enzyme. The enzyme may be a lysosomal hydrolase, including those listed in Table 1. In certain embodiments, the lysosomal hydrolase is chosen from, e.g., α-glucosidase, α-galactosidase A, and acid sphingomyelinase. In certain embodiments, the lyosomal hydrolase is GAA.

TABLE 1

Examples of LSDs and Corresponding Lysosomal Hydrolases

| Lysosomal Storage Disorder | Defective Enzyme |
|---|---|
| Fabry | α-Galactosidase A |
| Farber | Acid ceramidase |
| Fucosidosis | Acid α-L-fucosidase |
| Gaucher types 1, 2, and 3 | Acid β-glucosidase |
| $G_{M1}$ gangliosidosis | Acid β-galactosidase |
| Hunter (Mucopolysaccharidosis (MPS) II) | Iduronate-2-sulfatase |
| Hurler-Scheie, Hurler, Scheie (MPS I) | α-L-Iduronidase |
| Krabbe | Galactocerebrosidase |
| α-Mannosidosis | Acid α-mannosidase |
| β-Mannosidosis | Acid β-mannosidase |
| Maroteaux-Lamy (MPS VI) | Arylsulfatase B |
| Metachromatic leukodystrophy | Arylsulfatase A |
| Morquio A (MPS IV) | N-Acetylgalactosamine-6-sulfate sulfatase |
| Morquio B (MPS IV) | Acid β-galactosidase |
| Niemann-Pick A and B | Acid sphingomyelinase (ASM) |
| Pompe | Acid α-glucosidase (α-glucosidase; GAA) |
| Sandhoff | β-Hexosaminidase B |
| Sanfilippo A (MPS III) | Heparan N-sulfatase |
| Sanfilippo B (MPS III) | α-N-Acetylglucosaminidase |
| Sanfilippo C (MPS III) | Acetyl-CoA: α-glucosaminide N-acetyltransferase |
| Sanfilippo D (MPS III) | N-Acetylglucosamine-6-sulfate sulfatase |
| Schindler-Kanzaki | α-N-acetylgalactosaminidase |
| Sialidosis | Sialidase |
| Sly (MPS VII) | β-Glucuronidase |
| Tay-Sachs | β-Hexosaminidase A |

In certain embodiments, the glycoprotein may be a glycoprotein having at least 1, 2, 3, 4, 5, or more N-linked or O-linked glycosylated amino acid residues. In other embodiments, the protein may have 1, 2, 3, 4, 5 or more consensus sites for N-linked or O-linked glycosylation, at least one of which is glycosylated.

In certain embodiments, the protein may be a ligand for a receptor. For example, in some embodiments the protein may be a glycoprotein that binds to a receptor that recognizes a sugar such as, e.g., mannose or mannose-6-phosphate. In some embodiments, the glycoprotein may bind to, e.g., the asialoglycoprotein receptor, the cation-dependent mannose-6-phosphate receptor, the insulin-like growth factor II/cation-independent mannose-6-phosphate receptor, or the macrophage mannose receptor.

In certain embodiments, the protein is a glycoprotein that, when conjugated to an oligosaccharide comprising mannose-6-phosphate, is internalized more efficiently by a target cell (e.g., via CI-MPR-mediated endocytosis) than is the corresponding unconjugated glycoprotein. For example, the conjugated glycoprotein may be internalized more efficiently than the unconjugated glycoprotein by, e.g., at least 10%, 15%, 20%, 25%, 30%, 35%, 40%, 50%, 60%, 70%, 80%, or 90% (w/w) in a given time period. In other embodiments, at least 2, 3, 4, 5, 6, 7, 8, 9, or 10 fold (w/w) as much of the conjugated glycoprotein may be internalized, relative to the unconjugated glycoprotein, in a given time period. The referenced time period may be, for example, 10, 30, 45 minutes or 1, 2, 3, 5, 6, 12, 24, 48, or 72 hours, or more.

C. Methods of Coupling an Oligosaccharide to a Protein

The invention provides methods of coupling an oligosaccharide to a protein, such as, e.g., a glycoprotein. In one embodiment, the method comprises:
(a) providing an oligosaccharide comprising an aminooxy group;
(b) providing a protein having at least one carbonyl group; and
(c) reacting the aminooxy group of the oligosaccharide with the at least one carbonyl group of the protein, thereby coupling the oligosaccharide to the protein.

In certain embodiments, the methods further comprise adding a reducing agent to the coupled lysosomal enzyme. The reducing agent may be any reducing agent known to those of skill in the art, such as, e.g., sodium cyanoborohydride or sodium triacetoxyborohydride (STAB).

IV. OLIGOSACCHARIDE-PROTEIN CONJUGATES

The invention further provides an oligosaccharide-protein conjugate, comprising (1) a protein, (2) an oligosaccharide, and (3) an oxime group connecting the protein and the oligosaccharide. In some embodiments, the invention provides an oligosaccharide-protein conjugate prepared by the methods disclosed above. The oligosaccharide and protein components of the conjugate may be, for example, any oligosaccharide and protein described herein, wherein a conjugate thereof comprises an oxime group, as depicted below. (The oxime group depicted below is formally derived by reaction of an aminooxy group and an aldehyde group; oxime groups formally derived by reaction of an aminooxy group and a ketone group are also encompassed by this invention.)

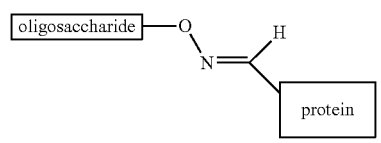

In certain embodiments, the oligosaccharide-protein conjugate is an oligosaccharide-glycoprotein conjugate. In certain embodiments, the oligosaccharide-protein conjugate is the conjugate of an oligosaccharide comprising at least one M6P and of a lysosomal hydrolase.

V. PHARMACEUTICAL COMPOSITIONS

This disclosure provides the use of a conjugate of the invention in the manufacture of a medicament for treating a lysosomal storage disorder. It also provides pharmaceutical compositions comprising an oligosaccharide-protein conjugate of the invention. In some embodiments, the pharmaceutical compositions of the invention comprise a conjugate of an oligosaccharide comprising at least one M6P and a lysosomal enzyme.

Pharmaceutical compositions of the invention may comprise one or more suitable pharmaceutical excipients. Standard pharmaceutical formulation techniques and excipients are well known to persons skilled in the art (see, e.g., 2005 *Physicians' Desk Reference®*, Thomson Healthcare: Montvale, N.J., 2004; *Remington: The Science and Practice of Pharmacy,* 20th ed., Gennado et al., Eds. Lippincott Williams & Wilkins: Philadelphia, Pa., 2000. The compositions may or may not contain preservatives. In some embodiments, pharmaceutical compositions comprising α-galactosidase A conjugates may comprise one or more excipients such as, e.g., mannitol, sodium phosphate monobasic monohydrate, and/or sodium phosphate dibasic heptahydrate. In some embodiments, pharmaceutical compositions comprising conjugates of α-glucosidase may comprise one or more excipients such as, e.g., mannitol, polysorbate 80, sodium phosphate dibasic heptahydrate, and sodium phosphate monobasic monohydrate.

The pharmaceutical composition may comprise any of the conjugates described herein either as the sole active compound or in combination with another compound, composition, or biological material. For example, the pharmaceutical composition may also comprise one or more small molecules useful for the treatment of a LSD and/or a side effect associated with the LSD. In some embodiments, the composition may comprise miglustat and/or one or more compounds described in, e.g., U.S. Patent Application Publication Nos. 2003/0050299, 2003/0153768; 2005/0222244; 2005/0267094.

The formulation of pharmaceutical compositions may vary depending on the intended route of administrations and other parameters (see, e.g., Rowe et al. *Handbook of Pharmaceutical Excipients,* 4th ed., APhA Publications, 2003.) In some embodiments, the composition may be a sterile, non-pyrogenic, white to off-white lyophilized cake or powder to be administered by intravenous injection upon reconstitution with Sterile Water for Injection, USP.

Administration of a pharmaceutical composition of the invention is not limited to any particular delivery system and may include, without limitation, parenteral (including subcutaneous, intravenous, intracranial, intramedullary, intraarticular, intramuscular, intrathecal, or intraperitoneal injection), transdermal, or oral (for example, in capsules, suspensions, or tablets). Administration to an individual may occur in a single dose or in repeat administrations, and in any of a variety of physiologically acceptable salt forms, and/or with an acceptable pharmaceutical carrier and/or additive as part of a pharmaceutical composition.

The conjugates described herein are administered in therapeutically effective amounts. Generally, a therapeutically effective amount may vary with the subject's age, condition, and sex, as well as the severity of the medical condition in the subject. The dosage may be determined by a physician and adjusted, as necessary, to suit observed effects of the treatment. Toxicity and therapeutic efficacy of such compounds can be determined by standard pharmaceutical procedures in vitro (i.e., cell cultures) or in vivo (i.e., experimental animal models), e.g., for determining the $LD_{50}$ (the dose lethal to 50% of the population) and the $ED_{50}$ (the dose therapeutically effective in 50% of the population). The dose ratio between toxic and therapeutic effects is the therapeutic index (or therapeutic ratio), and can be expressed as the ratio $LD_{50}/ED_{50}$. Conjugates that exhibit therapeutic indices of at least 1, 1.5, 2, 3, 4, 5, 6, 7, 8, 9, 10, and 20 are described herein. Conjugates that exhibit a large therapeutic index are preferred.

The data obtained from in vitro assays and animal studies, for example, can be used in formulating a range of dosage for use in humans. The dosage of such compounds lies preferably within a range of circulating concentrations that include the $ED_{50}$ with low, little, or no toxicity. The dosage may vary within this range depending upon the dosage form employed and the route of administration utilized. For any conjugate used in the present invention, the therapeutically effective dose can be estimated initially from in vitro assays. A dose may be formulated in animal models to achieve a circulating plasma concentration range that includes the $IC_{50}$ (i.e., the concentration of the test conjugate which achieves a half-maximal inhibition of symptoms) as determined in in vitro experiments. Levels in plasma may be measured, for example, by high performance liquid chromatography or by an appropriate enzymatic activity assay. The effects of any particular dosage can be monitored by a suitable bioassay of endpoints.

Unless otherwise indicated, conjugates of the invention may be administered at a dose of approximately from 1 μg/kg to 500 mg/kg, depending on the severity of the symptoms and the progression of the disease. For example, proteinaceous compounds may be administered by slow intravenous infusion in an outpatient setting every, e.g., 1, 2, 3, 4, 5, 6, 7, 8, 9, 10, or more days, or by, e.g., weekly, biweekly, monthly, or bimonthly administration. The appropriate therapeutically effective dose of a compound is selected by a treating clinician and would range approximately from 1 μg/kg to 500 mg/kg, from 1 μg/kg to 10 mg/kg, from 1 μg/kg to 1 mg/kg, from 10 μg/kg to 1 mg/kg, from 10 μg/kg to 100 μg/kg, from 100 μg to 1 mg/kg, and from 500 μg/kg to 5 mg/kg.

For example, conjugates of α-galactosidase A may be administered by intravenous infusion at a dose of, e.g., 1.0 mg/kg body weight every two weeks at an infusion rate of, e.g., less than or equal to 10, 13, 15, 16, 17, 18, 19, 20, 21, 22, 23, 24, 25, 26, 27, 28, 29, 30, 31, 32, or 33 mg/hour). In another example, conjugates of α-glucosidase may be administered intravenous injection at a dose of, e.g., 20 mg/kg or 40 mg/kg every two weeks, over approximately, e.g., 1, 2, 3, 4, 5, 6, 7, 8, 9, or 10 hours. In some embodiments, the rate of administration of α-glucosidase may be started at, e.g., 1 mg/kg/hr and then increased by, e.g., 2 mg/kg/hr every 30 minutes, after establishing patient tolerance to the infusion rate, until a maximum of, e.g., 7 mg/kg/hr. Additionally, examples of specific dosages may be found in the *Physicians' Desk Reference®*.

VI. METHODS OF TREATING LYSOSOMAL STORAGE DISORDERS

The invention provides methods of treating lysosomal storage disorders, such as, e.g., those disclosed in Table 1. In some embodiments, the invention provides the use of a conjugate described herein for treating a lysosomal storage disorder in a subject in need thereof. The invention further provides methods of targeting proteins to the lysosome by conjugation with oligosaccharides comprising mannose-6-phosphate.

In one embodiment, the method comprises administering to a mammal having a lysosomal storage disorder an oligosaccharide-glycoprotein conjugate of the invention in a therapeutically effective amount. The oligosaccharide-glycoprotein conjugate may be a conjugate of a lysosomal enzyme, such as a lysosomal enzyme listed in Table 1, with an oligosaccharide comprising mannose-6-phosphate. In one embodiment, the method comprises administering to a subject in need thereof a pharmaceutical composition comprising at least one of the conjugates described herein.

In certain embodiments, conjugates of the invention may be administered with one or more other therapies. The one or more other therapies may be administered concurrently with (including concurrent administration as a combined formulation), before, or after the administration of the conjugates of the invention.

In some embodiments, a patient may be treated (before, after, or during treatment with a conjugate of the invention) with an antipyretic, antihistamine, and/or immunosuppressant. In some embodiments, a patient may be treated with an antipyretic, antihistamine, and/or immunosuppressant prior to treatment with an oligosaccharide-glycoprotein conjugate of the invention in order to decrease or prevent infusion associated reactions. For example, patients may be pretreated with one or more of acetaminophen, azathioprine, cyclophosphamide, cyclosporin A, methotrexate, mycophenolate mofetil, oral steroids, or rapamycin.

In some embodiments, patients may be treated with one or more of acetaminophen, azathioprine, cyclophosphamide, cyclosporin A, methotrexate, mycophenolate mofetil, oral steroids, or rapamycin at or about, e.g., t=0 (the time of administration of the conjugate of the invention) and/or t=12, 24, 36, 48, 60, 72, 96, 120, and 144 hours for, e.g., the first 1, 2, 3, 4, 5, 6, 7, 8, 9, 10, or more incidences of treatment with a conjugate of the invention. For example, in some embodiments a patient with Fabry disease or Pompe disease may be treated with methotrexate (e.g., with 0.1, 0.2, 0.3, 0.4, 0.5, 0.6, 0.7, 0.8, 0.9, 1, 2, 3, 4, 5, 6, 8, 10, 12, 15, 25, 30, 35, 40, 50, 60, 70, 80 mg/kg methotrexate, or more) at or about, e.g., t=0, 24, and 48 hours for, e.g., the first 1, 2, 3, 4, 5, 6, 7, 8 weeks of treatment with a conjugate of the invention. In some embodiments, immune tolerance toward conjugates of the invention may be induced in a patient with a lysosomal storage disorder such as, e.g., mucopolysaccharidosis I, by treatment with cyclosporin A and azathioprine. For example, the patient may be treated with cyclosporine A and azathioprine as described in Kakkis et al., *Proc. Natl. Acad. Sci. U.S.A.* 101:829-834 (2004).

In some embodiments, a patient may be treated (before, after, or during treatment with a conjugate of the invention) with e.g., small molecule therapy and/or gene therapy, including small molecule therapy and gene therapy directed toward treatment of a lysosomal storage disorder. Small molecule therapy may comprise administration of one or more compounds described in, e.g., U.S. Patent Application Publication Nos. 2003/0050299, 2003/0153768; 2005/0222244; and 2005/0267094. Gene therapy may be performed as described in, e.g., U.S. Pat. Nos. 5,952,516; 6,066,626; 6,071,890; and 6,287,857 and U.S. Patent Application Publication No. 2003/0087868.

The terms "treatment," "therapeutic method," and their cognates refer to both therapeutic treatment and prophylactic/preventative measures. Thus, those in need of treatment may include individuals already having a particular lysosomal storage disease as well as those at risk for the disease (i.e., those who are likely to ultimately acquire the disorder or certain symptoms of the disorder).

A therapeutic method results in the prevention or amelioration of symptoms or an otherwise desired biological outcome, and may be evaluated by improved clinical signs or delayed onset of disease, increased activity of the metabolically defective enzyme, and/or decreased levels of the accumulated substrate of the metabolically defective enzyme.

The conjugates of the present invention are useful to treat various lysosomal storage disorders in humans or animals. For example, administration of the conjugates can be used to increase the deficient enzymatic activity in a patient, for example, by at least 10%. The increased enzymatic activity may be determined by, e.g., a reduction in clinical symptoms or by an appropriate clinical or biological assay.

GAA conjugates may be administered for the treatment of Pompe disease (also known as acid α-glucosidase deficiency, acid maltase deficiency, glycogen storage disease type II, glycogenosis II, and lysosomal α-glucosidase deficiency). Increased GAA activity may be determined by biochemical (see, e.g., Zhu et al., *J. Biol. Chem.* 279: 50336-50341 (2004)) or histological observation of reduced lysosomal glycogen accumulation in, e.g., cardiac myocytes, skeletal myocytes, or skin fibroblasts. GAA activity may also be assayed in, e.g., a muscle biopsy sample, in cultured skin fibroblasts, in lymphocytes, and in dried blood spots. Dried blood spot assays are described in e.g., Umpathysivam et al., *Clin. Chem.* 47:1378-1383 (2001) and Li et al., *Clin. Chem.* 50:1785-1796 (2004). Treatment of Pompe disease may also be assessed by, e.g., serum levels of creatinine kinase, gains in motor function (e.g., as assessed by the Alberta Infant Motor Scale), changes in left ventricular mass index as measured by echocardiogram, and cardiac electrical activity, as measured by electrocardiogram. Administration of GAA conjugates may result in a reduction in one or more symptoms of Pompe disease such as cardiomegaly, cardiomyopathy, daytime somnolescence, exertional dyspnea, failure to thrive, feeding difficulties, "floppiness," gait abnormalities, headaches, hypotonia, organomegaly (e.g., enlargement of heart, tongue, liver), lordosis, loss of balance, lower back pain, morning headaches, muscle weakness, respiratory insufficiency, scapular winging, scoliosis, reduced deep tendon reflexes, sleep apnea, susceptibility to respiratory infections, and vomiting.

In another aspect, conjugates of α-galactosidase A with oligosaccharides comprising M6P are administered for the treatment of Fabry disease. Fabry disease, or Anderson-Fabry disease, is a rare, X-linked, lysosomal storage disorder marked by a deficiency of α-galactosidase A, and results in accumulation of globotriaosylceramide (GL3) and other neutral glycosphingolipids in the lysosomes of visceral tissues and endothelial, perithelial, and muscle cells. Accumulation of the neutral glycosphingolipids in the vasculature results in narrowing and dilatation of the blood vessels, and ultimately to ischemia and infarction.

Administration of α-galactosidase A conjugates may result in a reduction in one or more clinical symptoms of Fabry disease including, e.g., acroparesthesia, angina, angiokeratoma, arrhythmia, ataxia of gait, burning and/or tingling pain in the hands and feet, cataracts, cold intolerance, conduction abnormalities, corneal whorling, coronary artery disease, dementia, depression, diarrhea, dilated cardiac chambers, dizziness, cardiomegaly, cardiomyopathy, diplopia, dysarthria, fatigue, fever with elevated erythrocyte sedimentation rate, hearing problems, heart disease, heart valve problems, heat intolerance, hemiataxia, hemiparesis, hypohidrosis, impaired sweating, infarction, ischemia, joint pain, kidney disease, left ventricular hypertrophy, lenticular abnormalities, lenticular opacity, lipiduria, muscle weakness, myocardial infarction, nausea, nystagmus, pain (e.g., intense pain radiating throughout the body), polydipsia, proteinuria, post-prandial pain, renal failure, retinal abnormalities, ringing in ears, stomach pain, ST-T wave changes, stroke, uremia, valvular disease, vertigo, vomiting, and weakness. Administration of α-galactosidase A conjugates may result in increased α-galactosidase A activity in, e.g., plasma, tears, leukocytes, biopsied tissues, or cultured skin fibroblasts. Administration of α-galactosidase A conjugates may also result in a histologic finding of a reduction (e.g., of at least 10%) or lack of increase of birefringent lipid globules. It may also result in a decrease in lipid globules in urinary sediment, improved renal function as measured by serum creatinine levels or creatinine clearance, and reduced proteinuria. Administration of α-galactosidase A conjugates may also result in a reduction in GL3 inclusions in the capillary endothelium of the kidney, heart, and skin. Additional assays for measuring efficacy of treatment for Fabry disease can be found in, e.g., MacDermott et al., *J. Med. Genet.* 38:750-760 (2001).

In yet another aspect, conjugates of acid sphingomyelinase are administered for treatment of Niemann-Pick disease, or acid sphingomyelinase deficiency. Administration of acid sphingomyelinase conjugates may result in a reduction in one or more clinical symptoms of Niemann-Pick disease including, e.g., abnormal cholesterol levels, abnormal lipid levels, ataxia, blood abnormalities, cherry red spots in the eye, frequent lung infections, growth retardation, hepatosplenomegaly, low numbers of platelets, lymphadenopathy, peripheral neuropathy, problems with lung function, shortness of breath, skin pigmentation changes, or xanthomas. In some embodiments, conjugates may be administered intracranially.

An alternative embodiment relates to treatment of mucopolysaccharidosis I (including, e.g., Hurler and Hurler-Scheie forms of MPS I) with conjugates comprising α-L-iduronidase. Administration of α-L-iduronidase conjugates may result in a reduction in one or more clinical symptoms of MPS I including, e.g., aortic regurgitation, aortic stenosis, carpal tunnel syndrome, chronic rhinitis, conductive hearing loss, constipation, corneal clouding, developmental delay, diarrhea, distended abdomen, dorsolumbar kyphosis, gibbus deformity of the back, hepatosplenomegaly, hydrocephalus, inguinal hernia, kyphosis, mental retardation, mitral regurgitation, mitral stenosis, night-blindness, open-angle glaucoma, poor hand function, progressive arthropathy, recurrent respiratory infections, respiratory insufficiency, retinal degeneration, scoliosis, sensorineural hearing loss, severe back pain, rhinorrhea, sleep apnea, spinal cord compression, thenar atrophy, umbilical hernia, and upper airway complications.

The foregoing and the following description are exemplary and explanatory only and are not restrictive of the invention, as claimed.

EXAMPLES

Examples 1-4 below describe the synthetic route depicted in FIG. 1. Compounds 1, 2, 3, and 4, as used below, have the chemical structures depicted in FIG. 1.

Example 1: Synthesis of Oligosaccharide 3

100 mg of oligosaccharide 1 (MW=1250; bisM6P-hydrazide, supplied by Biomira Inc., Edmonton, Canada) was dissolved in 15 ml of DMSO/$H_2O$ (50:50 in volume), yielding a 5.3 μmol/ml solution. 100 mg of t-Boc-aminooxy acetic acid tetrafluorophenyl ester 2 (Invitrogen Corp.; Carlsbad, Calif.; catalog #B3030) was dissolved in 7.5 ml of DMSO. 15 ml of the oligosaccharide solution was then mixed with 7.5 ml of the solution of 2 in a glass bottle, such that the molar ratio of compound 2:compound 1 in the resulting solution was 4:1. 744 μl of DHBt-OH (from a 32.06 mg/ml stock in DMSO) was added to the reaction mixture in a glass bottle, such that the final ratio of compound 2:DHBt-OH is 1:0.5. The mixture was gently shaken at room temperature (25° C.) at 100 RPM overnight for about 18 hours.

Figure 2A:
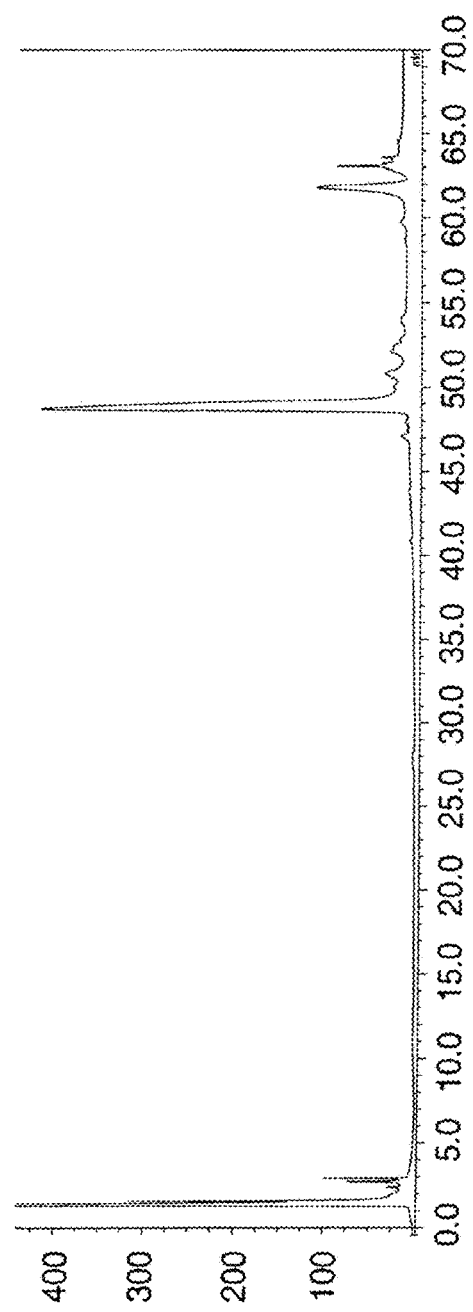
FIG. 2A is a Dionex analytical chromatograph of starting oligosaccharide 1.
Figure 2B:
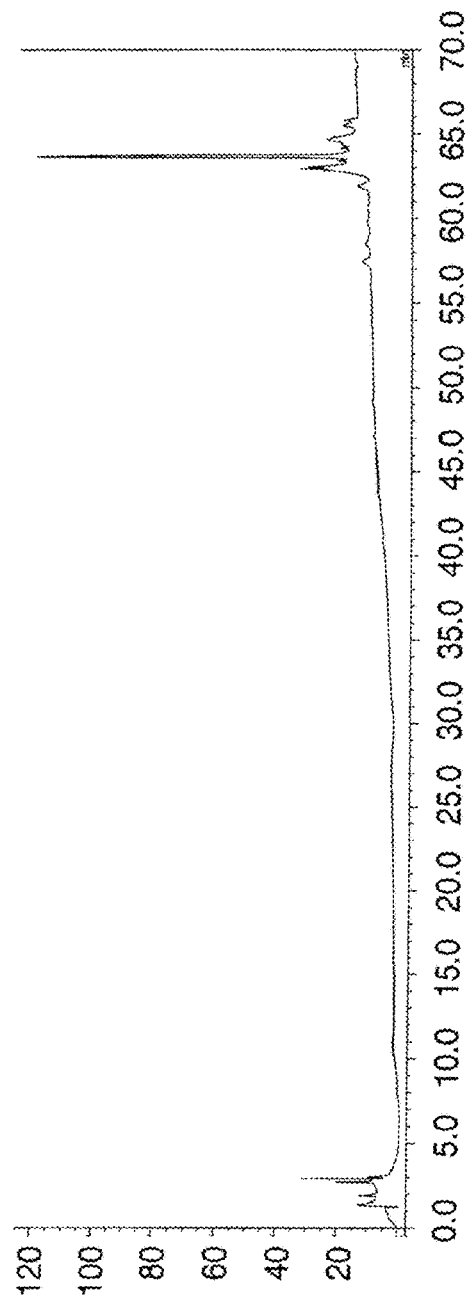
FIG. 2B is a Dionex analytical chromatograph of oligosaccharide 3.
Figure 2C:
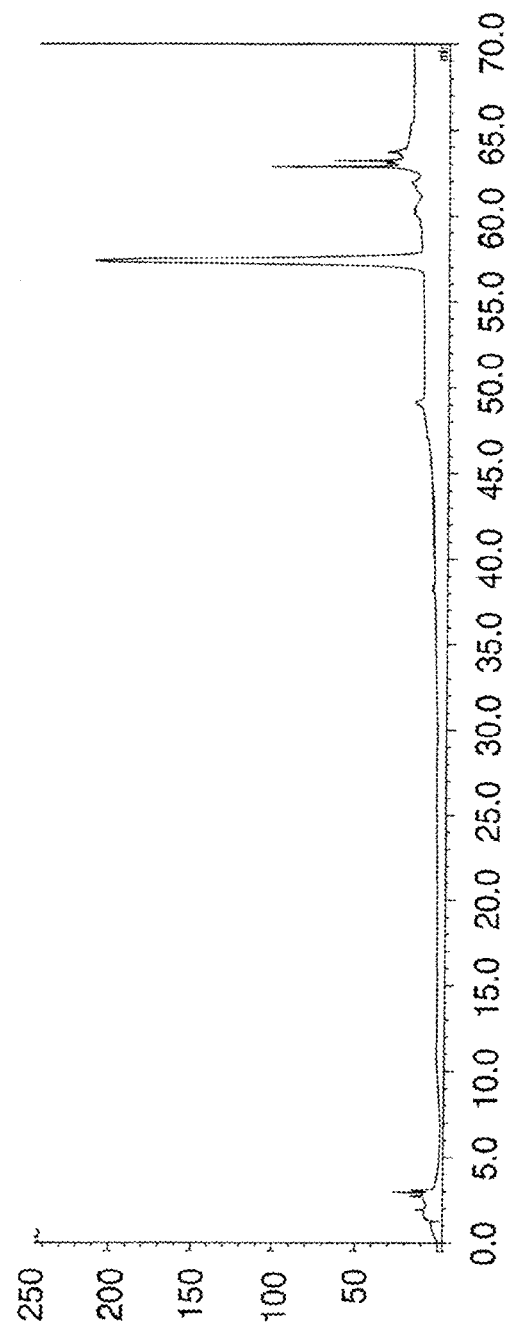
FIG. 2C is a Dionex analytical chromatograph of oligosaccharide 4.

The following morning, 10 μl of the reaction mixture was removed for Dionex analysis to confirm completion of the reaction. The results, depicted in FIG. 2, indicated 100% conversion from 1 to 3.

Example 2: Purification of Oligosaccharide 3

Method A.

The reaction mixture was diluted with an equal volume of $H_2O$ and dialyzed in dialysis tubing with molecular weight cutoff of 1000 Dalton (SpectraPor Inc.) twice against 4 L of $H_2O$ at 4° C. for at least 3 hours each. The samples were then lyophilized.

Method B.

A Sephadex G-10 gel permeation chromatography column with a bed volume of 225 ml was packed and equilibrated with deionized water. The reaction mixture was loaded onto the column, drained by gravity, and then eluted with deionized water at a flow rate of 75 ml per hour. 4.5 ml fractions were collected with a fraction collector. Fractions 10-23, which contained oligosaccharide 3, were collected, combined and lyophilized. The other small molecules, including t-Boc-AOAA, DHBt-OH, and DMSO, eluted in the later fractions, and were discarded.

Example 3: Deprotection of Oligosaccharide 3

The t-Boc group of the lyophilized sample was deprotected in 5 ml of 50% trifluoroacetic acid (TFA) in dichlormethane (DCM) in a glass bottle for 30 min with gentle shaking at 100 RPM. The TFA/DCM was then removed by a stream of $N_2$ in a chemical hood.

Example 4: Purification of Oligosaccharide 4

Method A.

After removing the TFA/DCM, the residue was dissolved in 10 ml of 0.5 M sodium acetate buffer, pH 5, and transferred to dialysis tubing with a molecular weight cutoff of 1000 Dalton. The bottle was washed with 4 ml of the same buffer, which was then transferred to the dialysis tubing. The sample was dialyzed twice against 3 L of 25 mM sodium acetate buffer, pH 7, for at least 3 hours, and then transferred to 4 L ice-cold $H_2O$ for overnight dialysis. The sample was recovered from the dialysis tubing and lyophilized.

Method B.

After removing the TFA/DCM, the residue was dissolved in 5 ml of 0.5 M sodium acetate buffer, pH 7.5, and loaded onto a Sephadex G-10 gel permeation chromatography column as in Example 2, Method B. The reaction mixture was loaded onto the column, drained by gravity, and then eluted with deionized water at a flow rate of 75 ml per hour. 4.5 ml fractions were collected with a fraction collector. Fractions 10-23, which contained purified oligosaccharide 4, were collected and lyophilized. A higher yield of oligosaccharide 4 was obtained upon purification by Method B than by Method A.

Figure 3A:
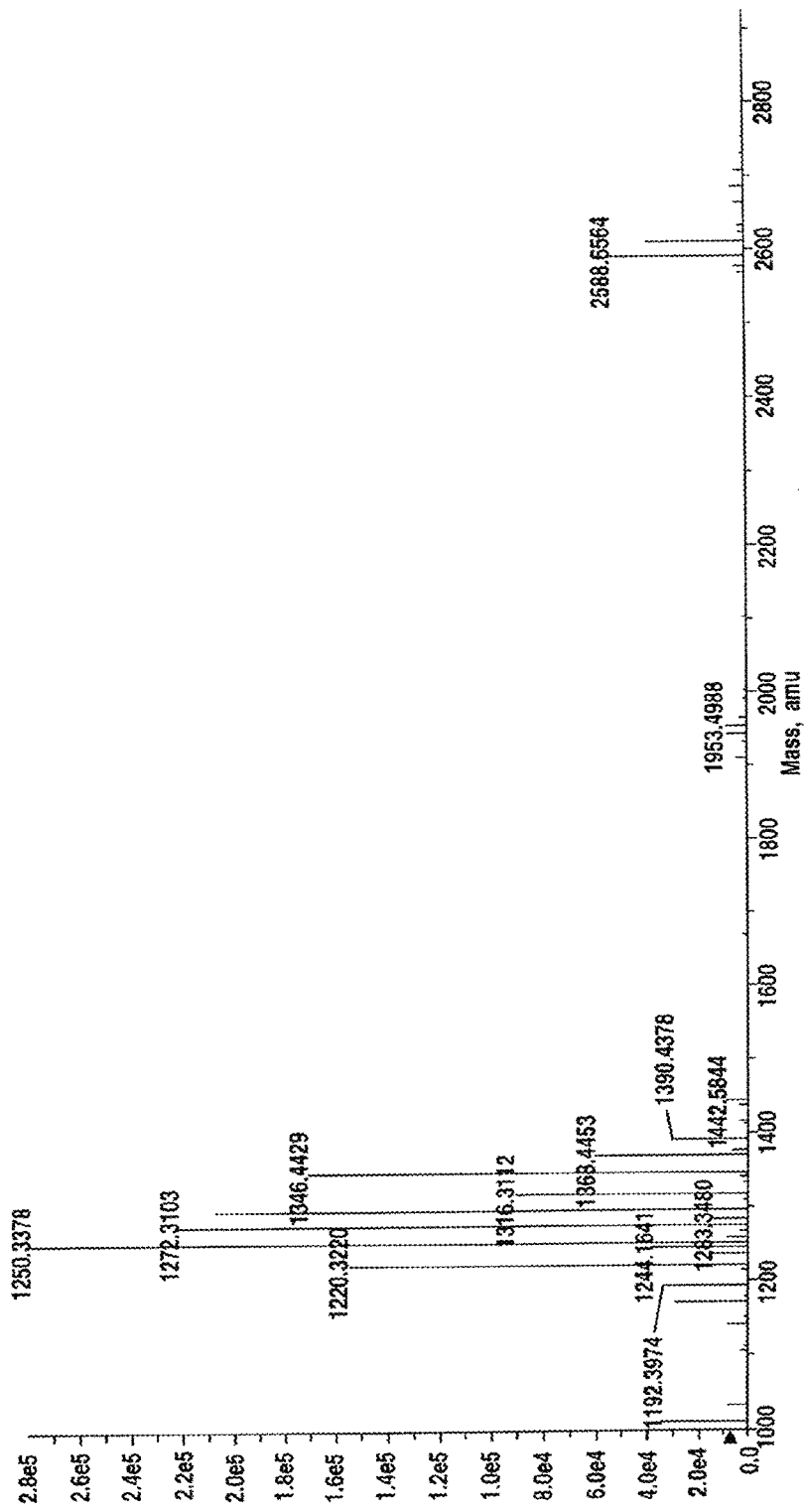
FIG. 3A is a mass spectrum of oligosaccharide 1 (calculated molecular weight=1250; calculated molecular weight of sodium salt=1338).
Figure 3B:
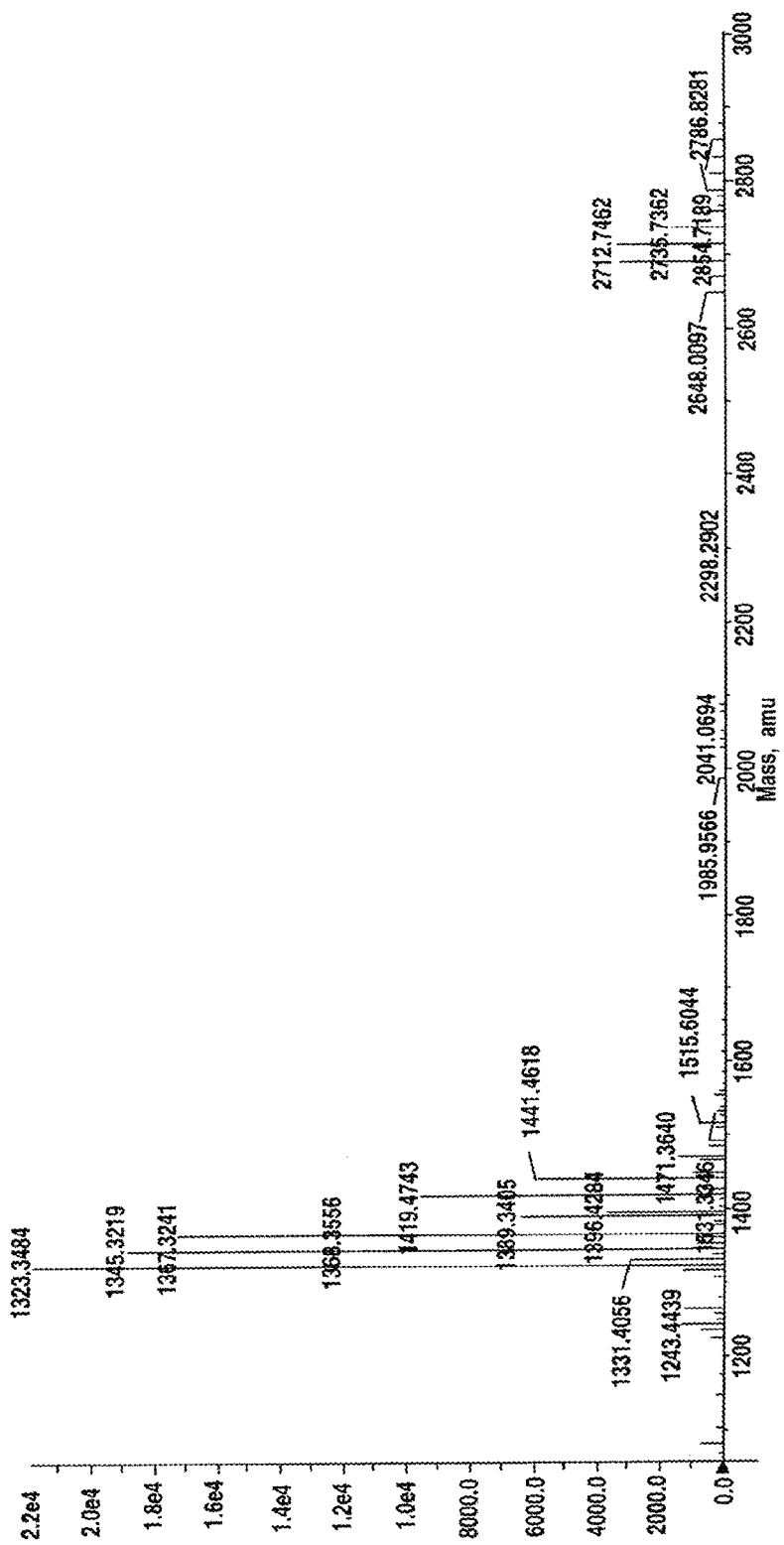
FIG. 3B is a mass spectrum of oligosaccharide 4 (calculated molecular weight=1323; calculated molecular weight of sodium salt=1411).
Figure 4:
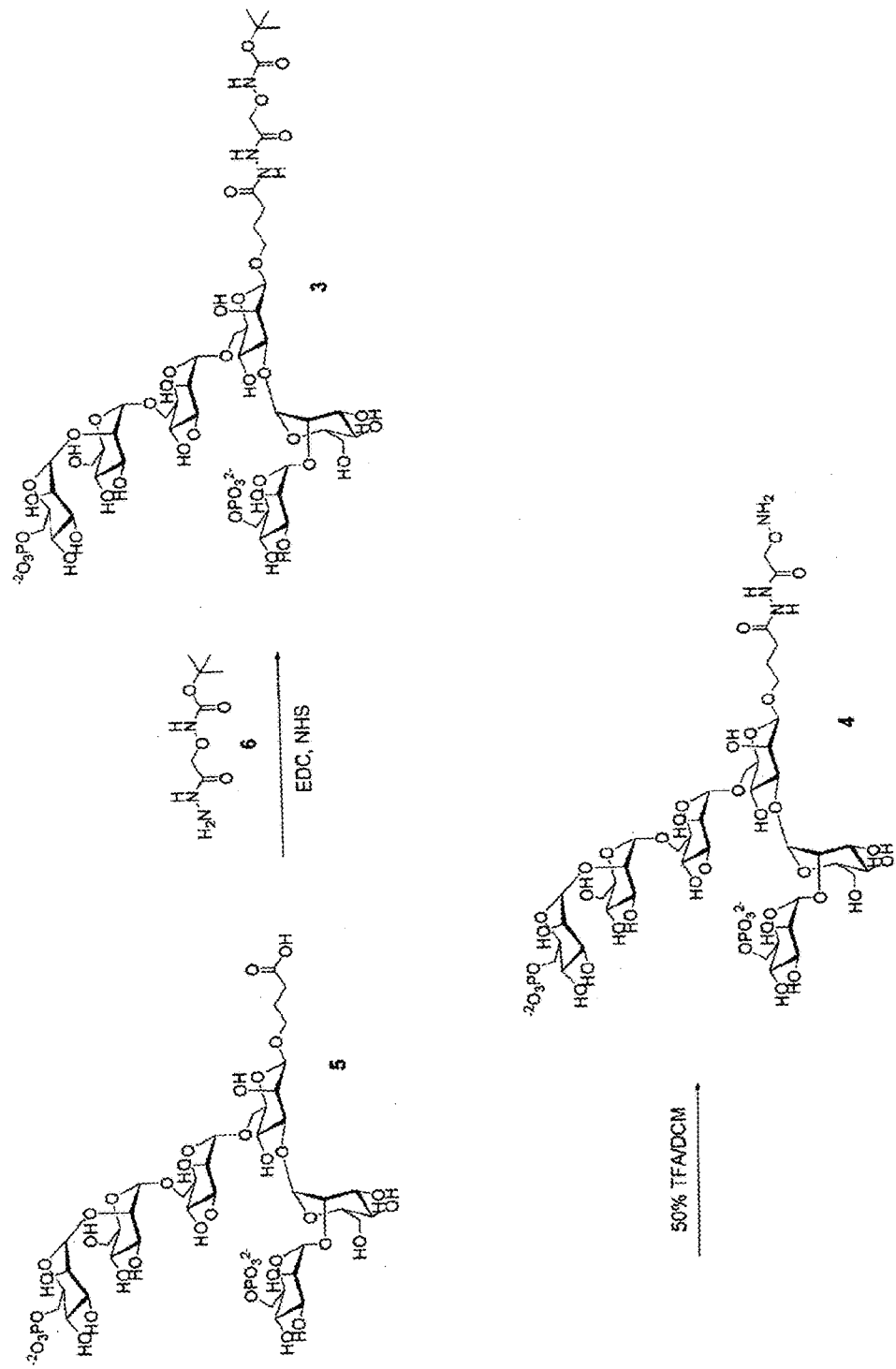
FIG. 4 is a reaction scheme depicting an illustrative embodiment of the methods of the invention. Oligosaccharide 5 having a first reactive group (a carboxyl group) is reacted with aminooxy compound 6 in presence of the coupling agent 1-ethyl-3-(3-dimethylaminopropyl)-carbodiimide (EDC) and the catalyst N-hydroxysuccinimide (NHS), to yield aminooxy-containing oligosaccharide 3. The Boc amino protecting group of oligosaccharide 3 is then removed with 50% TFA/DCM to yield oligosaccharide 4.

The final product obtained either from method B was analyzed by Dionex chromatography (FIG. 2C), and the identity of the product was confirmed by mass spectrometry (FIG. 3B). Some impurities were present in the spectra of FIG. 2C and FIG. 3B.

Example 5: Coupling of Oligosaccharide 4 to GAA

Oxidation of GAA.

Lyophilized recombinant human GAA (rhGAA) was reconstituted in $H_2O$ and dialyzed against 4 L of 100 mM acetate buffer (pH 5.6) 4 times to completely remove mannitol. After dialysis, the rhGAA was oxidized with 7.5 mM sodium periodate from 100 mM stock in 100 mM acetate buffer. After 30 minutes at 4° C. on ice, glycerol was added, and the sample was mixed on ice for 10 minutes to decompose excess sodium periodate. The oxidized material was then dialyzed against aqueous buffer (e.g., 100 mM sodium acetate) overnight.

Coupling.

A solution of oligosaccharide 4 in aqueous buffer (e.g., 100 mM sodium acetate, pH 5.6) was mixed with oxidized GAA and incubated at 37° C. for 4 hours to yield oligosaccharide-GAA conjugate 5. The reaction mixture was then diafiltered against 25 mM sodium phosphate buffer, pH 6.25, to remove unconjugated bisM6P glycan, and then adjusted with GAA formulation buffer (25 mM sodium phosphate buffer, pH 6.25, 2% mannitol, 0.005% Tween-80).

Example 6: Characterization of the GAA Conjugate

Detection of M6P.

The extent of oligosaccharide conjugation was measured by assaying conjugate 5 for binding to a M6P receptor column to which glycoproteins lacking M6P do not bind. Five micrograms of conjugate 5 were loaded onto a pre-equilibrated CI-MPR-Sepharose column (the column was prepared by coupling CI-MPR isolated from fetal bovine serum to Affigel-10), which was then washed with CI-MPR binding buffer for 11×2 mL fractions and eluted with CI-MPR binding buffer containing 5 mM M6P for 7×2 mL fractions. A total of 18 fractions were collected and assayed for enzymatic activity.

Monosaccharide Analysis.

Conjugate 5 is treated with 4N trifluoroacetic acid to hydrolyze the oligosaccharides, followed by high pH anion exchange chromatography with pulsed amperometric detection (PAD) on a BioLC liquid chromatography system (Dionex). The monosaccharide content is extrapolated from a monosaccharide standard curve using premixed monosaccharide standards (Dionex).

Specific Activity.

GAA activity is measured using a fluorometric assay in black 96-well microplates using 4-methylumbelliferyl-α-D-glucoside as a substrate. Dilutions of conjugate 5 are added in triplicate to a microtiter plate. 4-methylumbelliferyl-α-D-glucoside is added to each sample. The 96-well plate is incubated in a 37° C. incubator for 30 minutes. The release of product is detected fluorometrically, and compared to standard curves generated by measuring the fluorescence of a known quantity of a standard. The reaction is quenched by the addition of 125 μL of 1.0 M glycine-carbonate buffer, pH 10.5 to all wells. The specific activity is defined as nmol product released/hr/mg.

Internalization By L6 Myoblasts.

Cells (ATCC CRL-1458) were seeded into 6-well plates at $5.0 \times 10^5$ cells/well in growth media (DMEM+10% FBS) and grown to confluency. Cells were incubated with 0-100 nM GAA (conjugate 5 or unconjugated rhGAA) for 16 hours in DMEM+1% heat-inactivated-FBS+10 mM Hepes pH 6.7. After uptake, cells were washed with 3× PBS containing 5 mM M6P and lysed with 0.25% Triton X-100 for 1 hour on ice. Lysates were centrifuged at 18000 g for 5 minutes and tested for specific activity. See, e.g., Zhu et al., *J. Biol. Chem.* 279:50336-50341 (2004); Zhu et al., Biochem. J. 389:619-628 (2005).

All references cited herein are incorporated herein by reference in their entirety. To the extent publications and patents or patent applications incorporated by reference contradict the invention contained in the specification, the specification is intended to supercede and/or take precedence over any such contradictory material.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

The invention claimed is:

1. An oligosaccharide of Formula V:

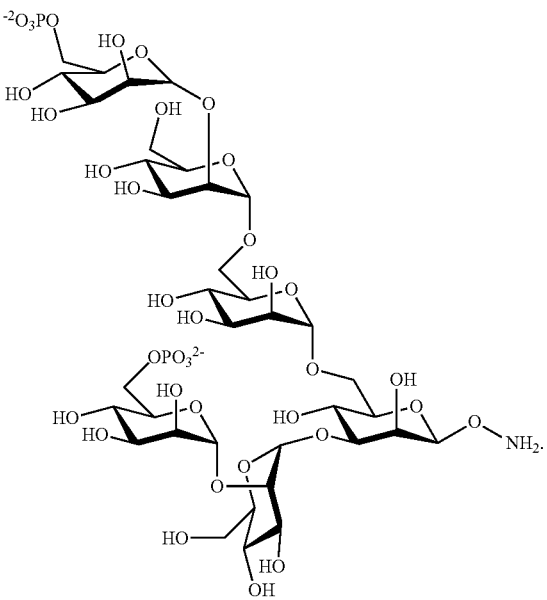

Formula V

* * * * *